US012788267B2

(12) United States Patent
Banerjee et al.

(10) Patent No.: US 12,788,267 B2
(45) Date of Patent: Nov. 10, 2026

(54) IDENTIFICATION OF SEIZURE ONSET ZONE IN FUNCTIONAL MAGNETIC RESONANCE IMAGING

(71) Applicants: Arizona Board of Regents on Behalf of Arizona State University, Tempe, AZ (US); Phoenix Children's Hospital, Inc., Phoenix, CA (US)

(72) Inventors: Ayan Banerjee, Gilbert, AZ (US); Sandeep Gupta, Phoenix, AZ (US); Varina Boerwinkle, Chapel Hill, NC (US)

(73) Assignees: Arizona Board of Regents on Behalf of Arizona State University, Tempe, AZ (US); Phoenix Children's Hospital, Inc., Phoenix, AZ (US)

( * ) Notice: Subject to any disclaimer, the term of this patent is extended or adjusted under 35 U.S.C. 154(b) by 245 days.

(21) Appl. No.: 18/474,098

(22) Filed: Sep. 25, 2023

(65) Prior Publication Data

US 2024/0099602 A1 Mar. 28, 2024

Related U.S. Application Data

(60) Provisional application No. 63/409,677, filed on Sep. 23, 2022.

(51) Int. Cl.

| | |
|---|---|
| ***A61B 5/055*** | (2006.01) |
| ***A61B 5/00*** | (2006.01) |
| ***G06T 7/00*** | (2017.01) |

(52) U.S. Cl.
CPC ............ *A61B 5/055* (2013.01); *A61B 5/0042* (2013.01); *A61B 5/4094* (2013.01); *G06T 7/0012* (2013.01); *G06T 2207/10088* (2013.01); *G06T 2207/20081* (2013.01); *G06T 2207/30016* (2013.01)

(58) Field of Classification Search
USPC ......... 128/920–925; 382/128–134, 154–228; 706/1–62, 900–903
See application file for complete search history.

(56) References Cited

U.S. PATENT DOCUMENTS

| | | | | |
|---|---|---|---|---|
| 12,193,825 B2 * | 1/2025 | Brinkmann | .......... | A61B 5/0006 |
| 2012/0253434 A1 * | 10/2012 | Nissila | ................. | A61N 5/0618 607/91 |

(Continued)

OTHER PUBLICATIONS

Michael Hutel; Apparatus And Method For Analysing MRI Data; 2019 (Year: 2019).*

(Continued)

*Primary Examiner* — Marcellus J Augustin
(74) *Attorney, Agent, or Firm* — Polsinelli PC

(57) ABSTRACT

A system and associated methods for accurate localization of seizure onset zone (SOZ) from independent components (IC) of resting state functional magnetic resonance imaging (rs-fMRI) to improve surgical outcomes in children with Drug Resistant Epilepsy (DRE) are disclosed. The system and methods define a phased approach, where fMRI noise-related biomarkers are used through high fidelity image processing techniques to eliminate noise ICs. Then SOZ markers are used through a maximum likelihood-based classifier to determine SOZ localizing ICs.

20 Claims, 7 Drawing Sheets
(6 of 7 Drawing Sheet(s) Filed in Color)

100

(56) References Cited

U.S. PATENT DOCUMENTS

| | | | | |
|---|---|---|---|---|
| 2014/0128762 | A1* | 5/2014 | Han | A61B 5/4064 600/544 |
| 2017/0113045 | A1* | 4/2017 | Baldassano | G16H 50/20 |
| 2018/0078150 | A1* | 3/2018 | Osorio | A61B 5/02055 |
| 2021/0169417 | A1* | 6/2021 | Burton | A61B 5/4857 |
| 2022/0248959 | A1* | 8/2022 | Neal | G01R 33/4806 |
| 2022/0338789 | A1* | 10/2022 | Elwood | A61B 5/372 |
| 2023/0052534 | A1* | 2/2023 | Stacey | A61N 1/36031 |
| 2023/0397876 | A1* | 12/2023 | Vieluf | A61B 5/746 |
| 2024/0021313 | A1* | 1/2024 | Alkaitis | G16H 40/63 |
| 2024/0415443 | A1 | 12/2024 | Gupta et al. | |

OTHER PUBLICATIONS

Arpan R. Chakraborty; Resting-State Functional Magnetic Resonance Imaging With Independent Component Analysis for Presurgical Seizure Onset Zone Localization: a Systen1atic Review and Meta-Analysis; 2020 (Year: 2020).*

Borbala Hunyadi; Automatic Selection of Epileptic Independent FMRI Components; 2025 (Year: 2025).*

Borbala Hunyadi; a Prospective FMRI-Based Technique for Localizing the Epileptogenic Zone in Presurgical Evaluation of Epilepsy; 2015 (Year: 2015).*

Ayan Banerjee; Automated Seizure Onset Zone Locator From Resting State Functional MRI in Drug Resistant Epilepsy; 2023 (Year: 2023).*

Boerwinkle, V. L. et al., Correlating Resting-State Functional magnetic resonance Imaging Connectivity by independent component analysis-based epileptogenic zones with intracranial electroencephalogram localized seizure onset zones; 2017 (Year: 2017).*

Lerman, R. I., et al., "A Note on the Calculation and Interpretation of the Gini Index," Economicas Letters 15, Feb. 6, 1984, pp. 363-368.

Lopes, R. et al., "Detection of epileptic activity in fMRI without recording the EEG," NeuroImage 60, Jan. 28, 2012, pp. 1867-1879.

Luckett, P. H., "Deep learning resting state functional magnetic resonance imaging lateralization of temporal lobe epilepsy," Epilepsia 63, Mar. 21, 2022, pp. 1542-1555.

Luders, H. O., et al., "The epileptogenic zone: general principles," Epileptic Disord. 8, pp. S1-S9.

Malmgren, K., et al., "Long-term outcomes of surgical treatment for epilepsy in adults with regard to seizures, antiepileptic drug treatment and employment," Seizure 44, Oct. 16, 2016, pp. 217-224.

Mayoral, M. et al., "Pileptogenic Zone Localization with FDG PET Using a New Dynamic Parametric Analysis," Frontiers Neurology 10, Apr. 17, 2019, pp. 1-9.

Mcintosh, A. M., "Temporal lobectomy: long-term seizure outcome, late recurrence and risks for seizure recurrence," Brain 127, Jun. 23, 2004, pp. 2018-2030.

Michaels, L. et al., "Developmental changes of BOLD signal correlations with global human EEG power and synchronization during working memory," PLoS ONE 7, Jul. 2012, vol. 7, Issue 7, pp. 1-13.

Moncrief, G. G., et al., "Self-rated executive dysfunction in adults with epilepsy and effects of a cognitive-behavioral intervention (HOBSCOTCH)," Epilepsy Behavior 121, May 28, 2021, pp. 1-6.

Murray, M. I. et al., "Cost of refractory epilepsy in adults in the USA," Epilepsy Research 23, Sep. 5, 1995, pp. 139-148.

Nagahama, Y. et al., "Intracranial EEG for seizure focus localization: evolving techniques, outcomes, complications, and utility of combining surface and depth electrodes," J. Neurosurgery 130, Jan. 15, 2018, pp. 1-13.

Nguyen, R. D., et al. "A comparison of machine learning classifiers for pediatric epilepsy using resting-state functional MRI latency data," Biomedical. Reports 15, Jul. 9, 2021, pp. 1-9.

Nissen, I. A. et al., "Localization of the Epileptogenic Zone Using Interictal MEG and machine learning in a large Cohort of Drug-Resistant Epilepsy Patients," Frontiers Neurology 9, Aug. 7, 2018, pp. 1-11.

Nozais, V., et al. "Deep learning-based classification of resting-state fMRI independent-component analysis," Neroinformatics 19, Feb. 5, 2021, pp. 619-637.

Ntolkeras, G. et al., "Presurgical accuracy of dipole clustering in MRI-negative pediatric patients with epilepsy: validation against intracranial EEG and resection," Clinical Neurophysiology 141, Mar. 26, 2021, pp. 126-148.

Perry, M. S. et al., "Surgical evaluation in children < 3 years of age with drug resistant epilepsy: patient characteristics, diagnostic utilization and potential for treatment delays," International League Against Epilepsy, Nov. 2, 2021, pp. 96-107.

Pindrik, J. et al. "Preoperative evaluation and surgical management of infants and toddlers with drug-resistant epilepsy," J. Neurosurgical, vol. 45, pp. 1-12.

Pizoli, C. E., et al., "Resting-state activity in development and maintenance of normal brain function," Proc. Natl. Acad. Sci. Biol. Sci., vol. 108, Jul. 12, 2011, pp. 11638-11643.

Prisco, L. et al. "A pragmatic approach to intravenous anaesthetics and electroencephalographic endpoints for the treatment of refractory and super-refractory status epilepticus in critical care," Seizure: European Journal Epilepsy 75, Sep. 23, 2019, pp. 153-164.

Roth, J. et al. "Epilepsy surgery in infants up to 3 months of age: safety, feasibility, and outcomes: a multicenter, multinational study," Epilepsia 62, Mar. 23, 2021, pp. 1897-1906.

Satzer, D. et al., "SEEG in 3D: Interictal Source Localization from Intracerebral Recordings," Frontiers Neurology Feb. 2022, pp. 1-11.

Schrouff, J. et al. "Brain functional integration decreases during propofol-induced loss of consciousness," NeuroImage 57, Apr. 16, 2011, pp. 198-205.

Shah, M. N. et al. "Resting state signal latency predicts laterality in pediatric medically refractory temporal lobe epilepsy," Childs Nervous System 34, Mar. 6, 2018, pp. 901-910.

Shah, M. N. et al. Role of resting state MRI temporal latency in refractory pediatric extratemporal epilepsy lateralization, JMRI. 49, Aug. 10, 2018, pp. 1347-1355.

Sillanpää, M. et al., "Long-term mortality in childhood-onset Epilepsy,". New England Journal Medicine, Dec. 23, 2010, pp. 363, 2522-2529.

Van Houdt, P. J. et al. "Are Epilepsy-Related fMRI Components Dependent on the Presence of Interictal Epileptic discharges in scalp EEG?," Brain Topogr. 28, Oct. 16, 2014, pp. 606-618.

Van Paesschen, W., et al., "The use of SPECT and PET in routine clinical practice in epilepsy," Current Opinion Neurology 20, 2007, pp. 194-202.

Von Oettzen, T. J., "PET and ictal SPECT can be helpful for localizing epileptic foci," Curr. Opin. Neurology, vol. 31, No. 2, Apr. 2018, pp. 184-191.

Wieser, H. G., "Proposal for a New Classification of Outcome with Respect to Epileptic Seizures Following Epilepsy Surgery," Epilepsia 42, Oct. 19, 2000, pp. 282-286.

Young, C. C., et al. "Pediatric functional hemispherectomy: operative techniques and complication avoidance," Neurosurgical Focus 48, Apr. 2020, pp. 1-10.

Zhang, C. H., "Lateralization and localization of epilepsy related hemodynamic foci using presurgical fMRI," Clinical Neurophysiology 126, Apr. 30, 2014, pp. 27-38.

Zhang, H. et al., "Resting-state functional MRI studies on infant brains: A decade of gap-filling efforts," NeuroImage 185, Jul. 7, 2018, pp. 664-684.

Banerjee, A. et al. "Automated seizure onset zone locator from resting-state functional MRI in drug-resistant epilepsy." Frontiers in Neuroimaging, Jan. 4, 2023, 22 pages.

Aaberg, K. M. et al., "Incidence and Prevalence of Childhood Epilepsy: a Nationwide Cohort Study," Pediatrics vol. 139, May 5, 2017, pp. 1-9.

Bandt, S. K.,et al. "The Role of Resting State Networks in Focal Neocortical Seizures," PLoS ONE vol. 9, Issue 9, Sep. 23, 2014, pp. 10.

Bansal, L. et al., "PET hypermetabolism in medically resistant childhood epilepsy: incidence, associations, and surgical outcome.," Epilepsia 57, Jan. 18, 2016, pp. 436-444.

(56) References Cited

OTHER PUBLICATIONS

Beckmann, C. F., et al., " Probabilistic Independent Component Analysis for Functional Magnetic Resonance Imaging," IEEE Transactions on Medical Imaging, vol. 23, No. 2, Feb. 2004, pp. 137-152.
Begley C. E. et al., "The Cost of Epilepsy in the United States: An Estimate from Population-Based Clinical and Survey Data," Epilepsia 41(3), Nov. 15, 1999, pp. 342-351.
Bhakta, K. et al., "Machine Learning Model Comparisons of User Independent & Dependent Intent Recognition Systems for Powered Prostheses," IEEE Robotics Automation Letters, vol. 5, No. 4, Oct. 2020.
Bharath, R. D.,et al. "Machine learning identifies "rsfMRI epilepsy networks" in temporal lobe epilepsy,". European Radiology 29, Feb. 8, 2019, pp. 3496-3505.
Boerwinkle, V. L. et al., "Network-Targeted Approach and Postoperative Resting State Functional MRI are associated with Seizure Outcome," Annals Neurology 86, Jul. 9, 2029, pp. 344-356.
Boerwinkle, V. L. et al., "Subcentimeter epilepsy surgery targets by resting state functional magnetic resonance imaging can improve outcomes in hypothalamic hamartoma," Epilepsia 59, Sep. 24, 2018, pp. 2284-2295.
Boerwinkle, V. L. et al., "Resting-state functional MRI Connectivity Impact on Epilepsy Surgery Plan and Surgical Candidacy: Prospective Clinical Work," Journal Neurosurgery Pediatric, Mar. 20, 2020, pp. 574-581.
Boerwinkle, V. L. et al., "Correlating Resting-State Functional magnetic resonance Imaging Connectivity by independent component analysis-based epileptogenic zones with intracranial electroencephalogram localized seizure onset zones and surgical outcomes in prospective pediatric in Prospective Pediatric Intractable Epilepsy Study,". Brain Connectivity vol. 7, No. 7, Nov. 7, 2017, pp. 424-442.
Bouyssi-Kobar, M. et al., "Altered Functional Brain Network Integration, Segregation, and Modularity in Infants Born Very Preterm at Term-Equivalent Age," Journal Pediatrics, vol. 213, Oct. 2019, pp. 13-21.
Bulacio, J. C.,et al. "Long-term seizure outcome after resective surgery in patients evaluated with intracranial electrodes," Epilepsia 53(10), Aug. 20, 2012, pp. 1722-1730.
Chakraborty, A. R., et al. "Resting-state functional magnetic resonance imaging with independent component analysis for presurgical seizure onset zone localization: a systematic review and meta-analysis," Epilepsia 61, Jul. 14, 2020, pp. 1958-1968.
Chen, Z., et al. "The value of resting-state functional magnetic resonance imaging for detecting epileptogenic zones in patients with focal epilepsy," PLoS ONE 12, Feb. 15, 2017, pp. 1-14.
Chibbaro, S., et al. "Pure endoscopic management of epileptogenic hypothalamic hamartomas," Neurosurg. Rev. 40, Feb. 17, 2017, pp. 647-653.
Cui, Y., et al. "Large scale Fine-Grained Categorization and Domain-Specific Transfer Learning," in Proceedings of the IEEE Conference on Computer Vision and Pattern Recognition (Salt Lake City), pp. 4109-4118.
D'Andrea, C. B. et al. "Real-time motion monitoring improves functional MRI data quality in infants.," Developmental . Cognitive Neuroscience 55, May 21, 2022, pp. 1-8.
Darki, F. et al., "The role of fronto-parietal and fronto-striatal networks in the development of working memory: a longitudinal study," Cerebral Cortex 25, Jun. 2015, 1587-1595.
Degeorge, E. G. et al. "Effects of age of onset and medication on cognitive performance and quality of life in patients with epilepsy," Epilepsy Behavior 121, May 15, 2021, pp. 1-7.
Desai, A. et al. "Interictal PET and ictal subtraction SPECT: sensitivity in the detection of seizure foci in patients with medically intractable epilepsy," Epilepsia 54, Oct. 2, 2012, pp. 341-350.
Dosenbach, N. U. F. et al. "Real-time motion analytics during brain MRI improve data quality and reduce costs" Neuroimage 161, Aug. 10, 2017, pp. 80-93.
Engel, J. "What can we do for people with drug-resistant epilepsy?," The 2016 Wartenberg Lecture. Neurology 87, Dec. 6, 2016, pp. 2483-2489.
England, M. J., et al., "Epilepsy across the spectrum: Promoting health and understanding. A Summary of the Insitute of Medicine reprot," Epilepsy & Behavior 25, Oct. 5, 2012, pp. 266-276.
Epilepsy Foundation, "Drug Resistant Epilepsy," Available online at: https://www.epilepsy.com/learn/drug-resistant-epilepsy (accessed Feb. 12, 2022).
Faghiri, A. et al., "Changing brain connectivity dynamics: from early childhood to adulthood," Hum Brain Map. 39, Nov. 13, 2017, pp. 1108-1117.
Foley, E. et al. "MEG detection of high frequency oscillations and intracranial-EEG validation in pediatric epilepsy surgery," Clinical Neurophysiology 132, Jun. 20, 2021, pp. 2136-2145.
Gonzalez-Martinez, J. A. et al., "Long-Term Seizure Outcome in Reoperation after Failure of Epilepsy Surgery," Neurosurgery 60, Jan. 5, 2007, pp. 873-880.
Greene, D. J. et al. "Behavioral interventions for reducing head motion during MRI scans in children," Neuroimage 171, Jan. 12, 2018, pp. 234-245.
Greve, D. N., et al., "Accurate and robust brain image alignment using boundary-based registration," Neuroimage 48, Jun. 30, 2009, pp. 63-72.
Griffanti, L. et al. "Hand classification of fMRI ICA noise components," Neuroimage 154, Dec. 16, 2016, pp. 188-205.
Griffanti, L. et al. "ICA-based artefact removal and accelerated fMRI acquisition for improved resting state network imaging," Neuroimage 95, Mar. 21, 2014, pp. 232-247.
Hunyadi, B. et al., "A prospective fMRI-based technique for localising the epileptogenic zone in presurgical evaluation of epilepsy," NeuroImage 113, Mar. 14, 2015, pp. 329-339.
Hunyadi, B. et al., "Automatic selection of epileptic independent fMRI components," Annual International Conference IEEE Eng. Medical Biol. Soc. 2014, pp. 3853-3856.
Hunyadi, B. et al., "ICA Extracts Epileptic Sources from fMRI in EEG-negative Patients: A Retrospective Validation Study," PLoS ONE, vol. 8, Issue 11, Nov. 2013.
Jenkinson, M. et al. "Improved Optimization for the Robust and Accurate Linear Registration and Motion Correction of Brain Images," NeuroImage 17, Sep. 19, 2001, pp. 825-841.
Jenkinson, M. et al. "A global optimisation method for robust affine registration of brain images. Medical Image," Analysis 5, Jan. 8, 2001, pp. 143-156.
Jiang, P. et al., "Functional connectivity of intrinsic cognitive networks during resting state and task performance in preadolescent children," PLoS ONE 13, Oct. 17, 2018, pp. 1-24.
Kaiboriboon, K., et al., "The Usefulness of Subtraction Ictal SPECT Coregistered to MRI in single- and Dual-Headed SPECT Cameras in Partial Epilepsy," Epilepsia 43, Jan. 28, 2002, pp. 408-414.
Kanner, A. M. et al., "Long-term seizure and psychiatric outcomes following laser ablation of mesial temporal structures," Epilepsia 63, Jan. 24, 2022, pp. 812-823.
Kasradze, S., L et al. "A six-year longitudinal study of neurocognitive problems in children with epilepsy," Brain & Development 43, Mar. 28, 2021, pp. 833-842.
Kelly, R. E., et al. "Visual inspection of independent components: defining a procedure for artifact removal from fMRI data," Journal Neuroscience Methods 189, Mar. 25, 2010, pp. 233-245.
Krizhevsky, A., et al., "ImageNet Classification with Deep Convolutional Neural Networks," Adv. Neural Information Processing Systems 25, vol. 60, No. 6, Jun. 2017, pp. 84-90.
Kwan, P. et al. "Definition of drug resistant epilepsy: consensus proposal by the ad hoc Task Force of the ILAE Commission on Therapeutic Strategies," Epilepsia 51, Nov. 3, 2009, pp. 1069-1077.
Kwan, P. et al. "Definition of refractory epilepsy: defining the indefinable?," Lancet Neurology, vol. 9, Nov. 13, 2009, pp. 27-29.
Kwan, P. et al. "The natural history of epilepsy: an epidemiological view," Journal Neurology Neurosurg. Psychiatr. 75, Jun. 29, 2004, pp. 1376-1381.
Laxer, K. D. et al. "The consequences of refractory epilepsy and its treatment," Epilepsy Behavior 37, Jun. 27, 2014, pp. 59-70.

(56) References Cited

OTHER PUBLICATIONS

Lee, K. H., et al., "Altered functional connectivity in seizure onset zones revealed by fMRI intrinsic connectivity," Neurology 83, Dec. 9, 2014, pp. 2269-2277.

Lee, K. H., et al., "Epilepsy surgery in children versus adults," J. Korean Neurosurg. Soc 62(3), Feb. 24, 2019, pp. 329-335.

* cited by examiner

100

200

300

400

500

600

IDENTIFICATION OF SEIZURE ONSET ZONE IN FUNCTIONAL MAGNETIC RESONANCE IMAGING

CROSS REFERENCE TO RELATED APPLICATIONS

This is a non-provisional application that claims benefit to U.S. Provisional Application Ser. No. 63/409,677, filed on Sep. 23, 2022, which is herein incorporated by reference in its entirety.

FIELD

The present disclosure generally relates to diagnosis and treatment of epilepsy including imaging techniques and computer-implemented evaluation; and more particularly, to systems and methods for an automated seizure onset zone locator from resting state functional MRI for drug resistant epilepsy.

BACKGROUND

Epilepsy is devastating, affecting 50 million worldwide (WHO). One in 150 children, 30% have drug resistant epilepsy (DRE) and causes significant morbidity and mortality. A consensus proposal by the ad hoc Task Force of the International League Against Epilepsy (ILAE) proposed the following definition for DRE: "a failure of adequate trials of two tolerated, appropriately chosen and used antiepileptic drug schedules (whether as monotherapies or in combination) to achieve sustained seizure freedom (considered as freedom from all seizures, including auras) for at least 12 months."

Early diagnosis and treatment of DRE can potentially avoid complications such as evolution into status epilepticus, and Sudden Unexplained Death in Epilepsy (SUDEP), wherein the individual dies due to cardio-respiratory failure from presumed nocturnal seizure activity. Moreover, in children, timely diagnosis, intensive management and treatment are pivotal in minimizing neurological damage. Further, the earliest onset of severe epilepsy in the neonatal population can lead to nearly constant life-threatening seizures requiring urgent need for surgical evaluation early in life.

It is with these observations in mind, among others, that various aspects of the present disclosure were conceived and developed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Corresponding reference characters indicate corresponding elements among the view of the drawings. The headings used in the figures do not limit the scope of the claims.

DETAILED DESCRIPTION

Figure 1:
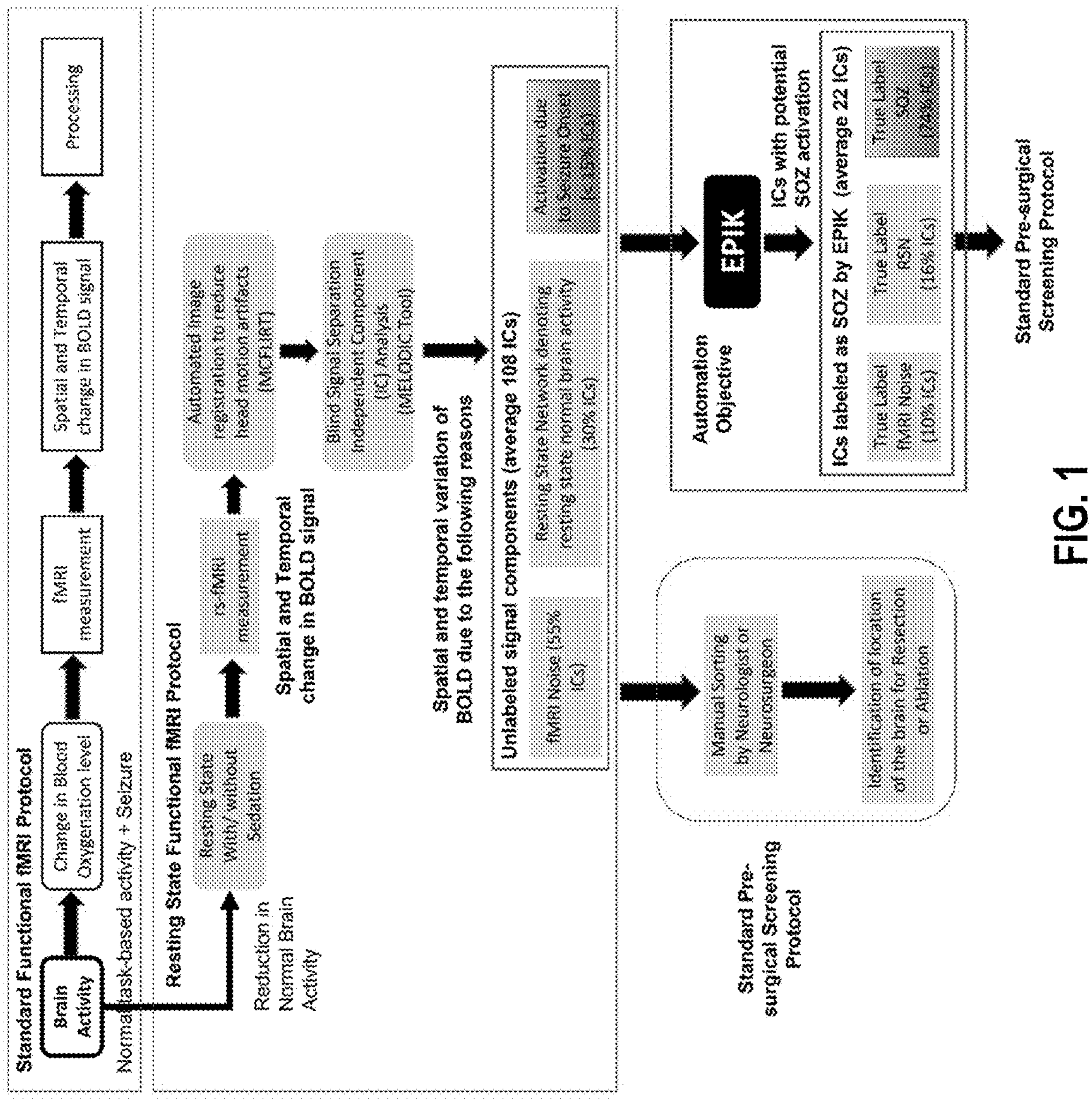
FIG. 1 is a flow diagram illustrating standard task-based fMRI protocol, resting state fMRI and data processing pipeline, standard rs-fMRI based pre-surgical evaluation of SOZ location, automation objective of EPIK, and advantages of EPIK in terms of reduction in manual processing requirements.

The present disclosure relates to systems and methods for accurate localization of seizure onset zone (SOZ) from independent components (IC) of resting state functional magnetic resonance imaging (rs-fMRI) to improve surgical outcomes in children with Drug Resistant Epilepsy (DRE). Automated IC sorting has limited success in identifying SOZ localizing ICs in adult normal rs-fMRI or uncategorized epilepsy. Children provide unique challenges due to the developing brain and associated surgical risks. The present concept proposes a novel SOZ localization algorithm (EPIK) for children with DRE.

Methods: EPIK is developed in a phased approach, where fMRI noise-related biomarkers are used through high fidelity image processing techniques to eliminate noise ICs. Then SOZ markers are used through a maximum likelihood-based classifier to determine SOZ localizing ICs. The performance of EPIK was evaluated on a unique pediatric DRE dataset (n=52). 24 children underwent surgical resection or ablation of rs-fMRI identified SOZ, concurrently evaluated with EEG and anatomical MRI. Two state-of-art techniques are used for comparison: a) least squares support vector machine, and b) Convolutional Neural Networks. The performance was benchmarked against expert IC sorting and Engel outcomes for surgical SOZ resection or ablation. Analysis is stratified across age and sex.

Results: EPIK outperforms state-of-art techniques for SOZ localizing IC identification with mean accuracy of 84.7% (4% higher), precision 74.1% (22% higher), specificity 81.9% (3.2% higher) and sensitivity 88.6% (16.5% higher). EPIK provides consistent performance across age and sex with best performance in <5-year age. It achieves a -5-fold reduction in the number of ICs to be potentially analyzed during pre-surgical screening.

Significance: Automated SOZ localization from rs-fMRI, validated against surgical outcomes, indicates potential for clinical feasibility. It eliminates the need for expert sorting, outperforms prior automated methods and is consistent across age, and sex.

Introduction and Technical Problems

As indicated above, epilepsy, and DRE in particular, is life-altering for most affected. Various conventional approaches for dealing with these afflictions shall now be described.

Surgery for DRE: The most effective treatment for DRE is surgery. Early surgery is key: "minimally invasive surgical treatment can be a life-changing option for DRE patients: hence management of SOZ requiring disconnecting techniques, or deep sited lesions requiring excision should be considered earlier rather than later". Notably, recent findings show that ultra-early (before 3 months old) surgical intervention in children evaluated to be DRE after trials of an average of 4 anti-seizure drugs, although seldom performed, has excellent epilepsy outcomes and leads to decrease in usage of anti-seizure drugs, without any increased risk of surgery related permanent morbidity.

Brain Imaging for Pre-surgical screening: Surgical intervention in DRE requires accurate localization of the seizure onset zone (SOZ) for success. Here we make a distinction between epileptic network (EN) and SOZ. EN denotes regions where seizure propagates and may be more extensive than the SOZ. As such it may be difficult as well as unnecessary to surgically eliminate EN since they can incorporate sensitive areas of the brain. Several brain imaging techniques has been explored to identify ictal seizure onset zone (SOZ), propagation zone (i.e., EN), and interictal activity (Table 1, below). This can be done with nuclear medicine-based imaging techniques such as positron emission tomography (PET) or ictal single-photon emission computerized tomography (SPECT). Recent works suggest some SOZ identification capability for PET and SPECT in both adults and children, however, accuracy heavily depends on the timing of the scan. Delay in drug infusion can result in detection of EN instead of SOZ. Invasive modalities such as intracranial EEG (iEEG) is considered as gold standard for SOZ identification and has shown excellent accuracy for both adults and pediatric DRE. Stereo-electroencephalography (SEEG) is minimally invasive which uses a three-dimensional configuration of depth electrodes to localize epileptiform activity and has shown some SOZ identification capability recently.

TABLE 1

Summary of brain imaging techniques and their application in SOZ identification for adults and children (PET—positron emission tomography, SPECT—single-photon emission computerized tomography, MEG—magnetoencephalography, iEEG—intracranial electroencephalography, fMRI—functional magnetic resonance imaging).

| Imaging Technique | Invasive/ Non-Invasive | Number of Imaging Sessions | Spatial Resolution | Temporal Resolution | Brain Area | SOZ ID in Adults with DRE | SOZ ID in children with DRE |
|---|---|---|---|---|---|---|---|
| PET | Invasive | 1 | 6 mm | 5 mins | Surface | Identified in 66.7% subjects | Only detects EN in 6.6% of patients and not SOZ |
| Ictal SPECT | invasive | 2, needs difference between ictal and inter-ictal SPECT | 6 mm | 15 mins | Surface | Detects EN and not SOZ | Detects EN and not SOZ |
| MEG | Non-invasive | 1 | 10-20 mm | <10 ms | Cortex | 75% accurate in 8 patients, 60% with ML in a large cohort | Poor concordance with SOZ. Identified onset zone is >20 mm distance from ground truth SOZ |
| iEEG (gold standard) | Invasive | Long term monitoring (14 days) | 6-8 cm | <5 ms | Cortex | 92.3% accurate | >90% accurate |
| fMRI | Non-Invasive | 1 | 3 mm | 2-5 s | Central Brain | Sensitivity 83% and specificity 67% | 89% accurate SOZ identification |

However, traditional analysis of PET, SPECT, or SEEG is relatively temporally and spatially restricted, whereas functional interpolation of brain activity might allow for noninvasive three-dimensional representation of epileptiform activity and avoid pitfalls inherent of other modalities (Table 1). Recently, magnetoencephalography (MEG) and functional magnetic resonance imaging (fMRI) based noninvasive techniques have been analyzed for DRE in both adults and children and show descent SOZ identification capability. A combination of MEG and fMRI imaging is also proposed for accurate SOZ identification. However, a major drawback of such brain imaging based SOZ identification techniques is the heavy reliance on manual sorting of images and their components, which not only increases cost but also reduces accessibility and repeatability.

Unfortunately, less than 1% of DRE patients are evaluated for surgery and only 25% of those undergo surgery, part due to the diagnostic and surgical treatment high expensive (>$200,000/patient) and risk of debilitating impairment. Of the 1% evaluated, surgical failure rates are 30-70% despite the use of noninvasive SOZ-localization biomarkers such as anatomical MRI, scalp EEG, simultaneous EEG-fMRI, and magnetoencephalography which are then often confirmed by invasive iEEG. Hence, for surgery to be safe and efficient for wide acceptance, accessible, minimally invasive and accurate SOZ localization is essential.

One of the newer methods showing promise, to this end, is resting state functional MRI (rs-fMRI). Rs-fMRI has shown accurate SOZ-localization capacity by various analysis approaches, but only independent component analysis (ICA) has provided Level 1 evidence and has led to improvement in surgical outcomes and candidacy in DRE. However, expert interpretation of independent components (IC) into sources of noise, normal resting state networks (RSN), and SOZs, limits reproducibility and availability. An automated whole-brain data-driven SOZ-localizing IC identification technique that is rigorously validated against surgical destruction outcomes, reproducible, equally effective across age and sex and epilepsy subtype may greatly improve epilepsy care feasibility, morbidity, and mortality.

Proposed Solution to Technical Problems fMRI based screening: Referring to flow diagram 100 of FIG. 1, functional MRI (fMRI) is a popular imaging technique originally used to identify brain activity in terms of blood oxygenation level change in different parts of the brain for a given mental task. However, for SOZ detection, it is required to identify blood oxygenation changes due to onset of seizure. Hence, an important step is to remove other sources of brain activity such as mental tasks, fMRI noise, and head motion. Rs-fMRI requires the subject to be in resting state, which is achieved in majority of children through sedation. Even if any mental task is eliminated there are still resting state brain activity in a subject, which are manifested as RSN brain activity. Head motion is a significant source of noise. Although head motion is limited to less than 1 mm it still can pose significant amount of noise in the rs-fMRI measurement. Automated image registration is used to reduce head motion artifacts in rs-fMRI (FIG. 1 middle panel). The resulting rs-fMRI captures brain activity due to several sources including, a) noise (fMRI machine noise and head motion), b) RSN (resting state activity of the brain), and c) SOZ (change in blood oxygenation due to seizure onset). To decouple the effects of noise, RSN and SOZ in rs-fMRI signals, ICA is used to recover mutually independent fMRI signal components (ICs) that potentially only captures brain activity from one of the three sources.

Rs-fMRI ICA results in approximately 100 ICs. Each IC is a spatial-temporal distribution of regions of synchronous activity. In ICA of those with DRE, there are three IC categories: 1) RSNs which are well described and validated in the literature; 2) SOZ, currently, highly dependent on expert sorting; and 3) noise, which is also well understood, resulting from cardiovascular, cerebral-spinal-fluid-pulsation, or scanner artifacts (as described in Boerwinkle et al. 2017 for details and examples). In standard rs-fMRI based pre-surgical screening for DRE children, the entire set of ICs is analyzed by a neurosurgeon or neurologist to determine which ICs capture blood oxygenation changes due to seizure onset. Such an IC is referred to as a “SOZ localizing IC”. The neurosurgeon then determines the location of seizure onset in the brain using the SOZ localizing IC and a recommendation for surgical procedure such as resection or ablation or neurostimulation is made.

Given that ICA results in >100 ICs and only <10% are SOZ localizing ICs, manual sorting of rs-fMRI ICs to search for SOZ localizing IC is a significant time commitment by the neurosurgeon resulting in increased cost, reduces availability, and higher chance of false positives (FIG. 1). In some examples, the present inventive concept disclosed herein focuses on automating the task of IC sorting and reducing the number of ICs to be analyzed by the neurosurgeon for pre-surgical evaluation for children with DRE.

Automation of fMRI-based screening: Recent works have considered two automation objectives with rs-fMRI (Table 2): a) classification of subjects with or without epilepsy by identifying epilepsy networks using rs-fMRI BOLD signal z score latency maps, and b) localization of seizure onset zone using rs-fMRI ICs. Epilepsy networks indicate the areas of the brain that are affected by the propagation of seizure. As such they may not indicate the origin of the seizure, which is encapsulated by SOZ. Our work in this paper, tackles the second automation objective of SOZ localization.

Automated classification of rs-fMRI ICs as SOZ or RSN has been explored using supervised shallow machine learning (ML), and using deep learning (DL) in healthy adults to identify the typical RSNs, and is yet to be tested in epilepsy (Table 2 below). Supervised ML indicates that the DRE population has to be divided into two parts: a) training set, which is used to configure the ML, and b) testing set, which is used to test the performance of the ML. Some supervised ML can also choose to utilize a validation set. The performance of the ML technique on the validation set is used to update the training process and improve the performance in the validation set. Hence, the performance on the validation set is excluded from the analysis in Table 2 and only the test set performance is reported. Recent automated methods to classify adult rs-fMRI into RSN, SOZ and noise ICs are of three types: 1) Voxel-based network measures quantifying the number of connections to each voxel in an IC, called voxel degree connectivity (VDC), as indicators for SOZ. Such approaches have small sample size ($n \approx 20$) and show maximum reported sensitivity of 77% and specificity of 57% (Table 2); 2) ML based classification, with a sensitivity of 40% and specificity of 77%; and 3) DL approaches for only identifying RSN and noise, but not SOZs, for normal and non-DRE epileptic patients (accuracy 92% in Table 2).

To date, automated approaches have not been successful in classification of RSN, noise, and SOZ, in rs-fMRI for pediatric DRE patients due to challenges including: 1) Lack of normalized pathological rs-fMRI RSN data for children; 2) Databases with balanced instances of RSN, SOZ and noise, large enough for DL techniques to effectively recognize the three IC categories are not available; 3) Potentially inadequate performance of SOZ identification in children with DRE can indicate high risk of developmental disorders post-surgery. Given that each patient only has 5% ICs as SOZ, a 40% sensitivity means only two out of five SOZ ICs are correctly identified, while 14 are wrongly identified as SOZ; and 4) fMRI-based pre-surgical mapping is more complicated for children with DRE due to developmental changes during cognitive maturation, the impairment experienced due to DRE and the normal representation of memory function during development, which may differ from adults. Hence, the efficacy of fMRI classification techniques on adults needs to be reexamined for children with DRE.

TABLE 2

Comparison of related research highlighting innovative aspects of the proposed research (DL deep learning, DRE drug resistant or intractable epilepsy, EEG-fMRI simultaneous EEG and functional MRI, IC independent component, ID identification, iEEG intracranial EEG, ML machine learning, LS-SVM least squares support vector machine, VDC voxel degree connectivity, CNN convolutional neural network)

| | | Epilepsy type, epileptic zone indicators, task objective, and validation modality | | | | Automation technique explored | |
|---|---|---|---|---|---|---|---|
| Problem | Study | Epilepsy type | SOZ (S), RSN (R), Epilepsy Network (EN)', Not Specified (NS) | Task Objective | Primary Outcome validation modality | Machine Learning Technique | Supervised (Sup)/ Unsupervised (U) |
| Detection of Epilepsy | Nguyen 21 (Nguyen RD, 2021) | DRE | EN | Epilepsy classification using fMRI z score latency | Seizures | CNN | Sup |
| | Lopes 2012 (R. Lopes, 2012) | Focal | NS | Epilepsy classification using BOLD time series | Seizures | Time series analysis | U |
| | Bharath 2019 (Bharath, 2019) | Focal Temporal Lobe | Hand classification EN | Epilepsy classification using ICA | Seizures | SVM | Sup |
| Pre-Surgical Screening to Determine Seizure Onset Zone (SOZ) | Boerwinkle 2017 (Boerwinkle VL M. D., 2017) | DRE | R & S | Manual SOZ localization | iEEG and post-op seizure | No automation | Sup |
| | Shah 2018 (Shah MN, 2018) | DRE | NS | Finding correlation between fMRI z score latency and seizure freedom | Post-op Seizure | Statistical correlation measures | U |
| | Shah 2019 (Manish N Shah, 2019) | DRE | NS | fMRI z score latency-based seizure foci lateralization | Manual lateralization | Statistical correlation measures | U |
| | Hunyadi 2014 (Borbala hunyadi, 2015) | DRE | S | Automated SOZ identification (ID) | EEG-fMRI | LS-SVM | Sup |
| | Zhang 2015 (Clara Huishi Zhang, 2015) | DRE | S | SOZ localization with manual determination of brain boundary | Concordance with surgery resection | Statistical methods using thresholds | U |
| | Lee 2014 (Lee, 2014) | Intractable partial | S | VDC based SOZ localization | iEEG. | Statistical methods on time series | U |
| | Nozais 21 (Victor Nozais, 2021) | Healthy | R | DL based RSN ID | Manual IC Sorting | MLP | Sup |
| | Luckett 2022 (Patrick H. Luckett, 2022) | Focal Temporal Lobe | R & S | DL based SOZ hemisphere ID | Hemispheres lateralization of SOZ, and RSNs | CNN | Sup |
| | EPIK (current study) | DRE | R & S | Fully automated unsupervised method (EPIK) | Manual IC Sorting Comparison of Hunyadi et al and Nozais et al on the same dataset; and post-op seizures | Rule guided noise elimination, maximum likelihood based classification | U |

TABLE 2-continued

Comparison of related research highlighting innovative aspects of the proposed research (DL deep learning, DRE drug resistant or intractable epilepsy, EEG-fMRI simultaneous EEG and functional MRI, IC independent component, ID identification, iEEG intracranial EEG, ML machine learning, LS-SVM least squares support vector machine, VDC voxel degree connectivity, CNN convolutional neural network)

| | | | Epilepsy Dataset | | | | |
|---|---|---|---|---|---|---|---|
| Problem | Study | Automation technique explored Performance | N | C child A adult | N of epilepsy Subjects (N with DRE) | N of test epilepsy subjects | N of of subjects with surgical outcomes |
| Detection of Epilepsy | Nguyen 21 (Nguyen RD, 2021) | Accuracy in Epilepsy identification = 74% Sensitivity = 85% Specificity = 71% | 322 | C | 63 (63) | 13 | 0 |
| | Lopes 2012 (R. Lopes, 2012) | Accuracy = 87.5% | 15 | A | 15 (0) | 15 subjects with 40 events | 0 |
| | Bharath 2019 (Bharath, 2019) | Accuracy = 97.5% Sensitivity = 100% Specificity = 94.4% | 132 | A | 42 (0) | 0 (No test data, cross validation accuracy) | 0 |
| Pre-Surgical Screening to Determine Seizure Onset Zone (SOZ) | Boerwinkle 2017 (Boerwinkle VL M. D., 2017) | 89% accuracy | 40 | C | 40 (40) | 33 | 40 |
| | Shah 2018 (Shah MN, 2018) | 25 out of 26 subjects have temporal lobe signal latency | 26 | C | 26 (26) | 26 | 26 (21 seizure free) |
| | Shah 2019 (Manish N Shah, 2019) | Mean accuracy 70% Mean sensitivity 85% Mean Specificity 65% | 38 | C | 38 (38) | 38 | 38 (14 seizure free) |
| | Hunyadi 2014 (Borbala hunyadi, 2015) | 40% sensitivity 77% specificity | 18 | A | 18 (18) | 10 | Not Specified (NS) |
| | Zhang 2015 (Clara Huishi Zhang, 2015) | 77.7% sensitivity* 57% specificity** | 9 | A | 9 (9) | 9 | NS |
| | Lee 2014 (Lee, 2014) | 72.4% sensitivity*** | 29 | A | 29 (29) | 21 | 29 (2 seizure free) |
| | Nozais 21 (Victor Nozais, 2021) | 92% accuracy | 2000 | A | 0 (0) | 0 | 0 |
| | Luckett 2022 (Patrick H. Luckett, 2022) | 90.6% accuracy ***** | 2164 | A | 32 (0) | 32 | 15 (11 seizure free) |

TABLE 2-continued

Comparison of related research highlighting innovative aspects of the proposed research (DL deep learning, DRE drug resistant or intractable epilepsy, EEG-fMRI simultaneous EEG and functional MRI, IC independent component, ID identification, iEEG intracranial EEG, ML machine learning, LS-SVM least squares support vector machine, VDC voxel degree connectivity, CNN convolutional neural network)

| | | | | | | | |
|---|---|---|---|---|---|---|---|
| | EPIK (current study) | RSN success: Specificity: 73.7% Sensitivity: 72% SOZ success: Specificity: 81.9% Sensitivity: 88.6% | 52 | C | 52 (52) | 52 | 24 (18 seizure free) |

*Zhang 2015 only mentions concordance with surgical resection. Concordance is assumed to be true positive, and failure is assumed to be false negative. Hence percentage concordance is assumed to be sensitivity.
**Zhang 2015 mentions success in rejecting non-epilepsy related IC. Rejection of non-epilepsy IC is assumed to be true negative and failure to reject is assumed to be false positive. Hence success rate is specificity.
***Lee 2014 defines accordance with ic EEG. Accordance is assumed to be true positive, and failure is assumed to be false negatives. Hence percentage accordance is assumed to be sensitivity.
**** "significant" exact degree of significance not reported.
***** Sensitivity and specificity not mentioned. The high accuracy could also be due to the presence of large number of true negatives.
†Epileptic Networks were those found to be altered compared to healthy controls, however, were not identified as being causative of epilepsy or a seizure onset zone.

Most current studies (Table 2) focus on adult epilepsy with unknown effect of the degree of hypothesized network disruption effect on localization. Currently available automated IC sorting techniques either only identify SOZ or RSN localizing ICs. Hunyadi et al., the first major work to attempt SOZ localizing ICs identification, used supervised ML but could only achieve a specificity of 77% and sensitivity of 40% on a subset of adult patient population. A more recent technique by Nozais et al. used DL to identify only RSN in healthy adults and reports an accuracy of 92%. The major drawback of DL techniques is the requirement for labelled data on all three IC categories. Table 2 shows that such labelled data is rarely available, even if we combine datasets from different authors, IC data labelled as RSN and SOZ is only available from 212 DRE children. For DL to successfully recognize SOZ it will need at least a balanced distribution of RSN and SOZ. The DL works in this domain utilize RSN data from 2000 healthy subjects for appropriate training (Table 2 Nozais et al and Luckett et al). Hence to achieve balanced data, we would need SOZ from at least 2000 subjects which is not available currently.

There has been one prior unsupervised approach by Zhang et al., however, it was applied to DRE adults and achieved a sensitivity of 78% and specificity of 57%. We cannot replicate that study for this paper, because specific information about parameter settings were not discussed in Zhang et al.

Figure 2:
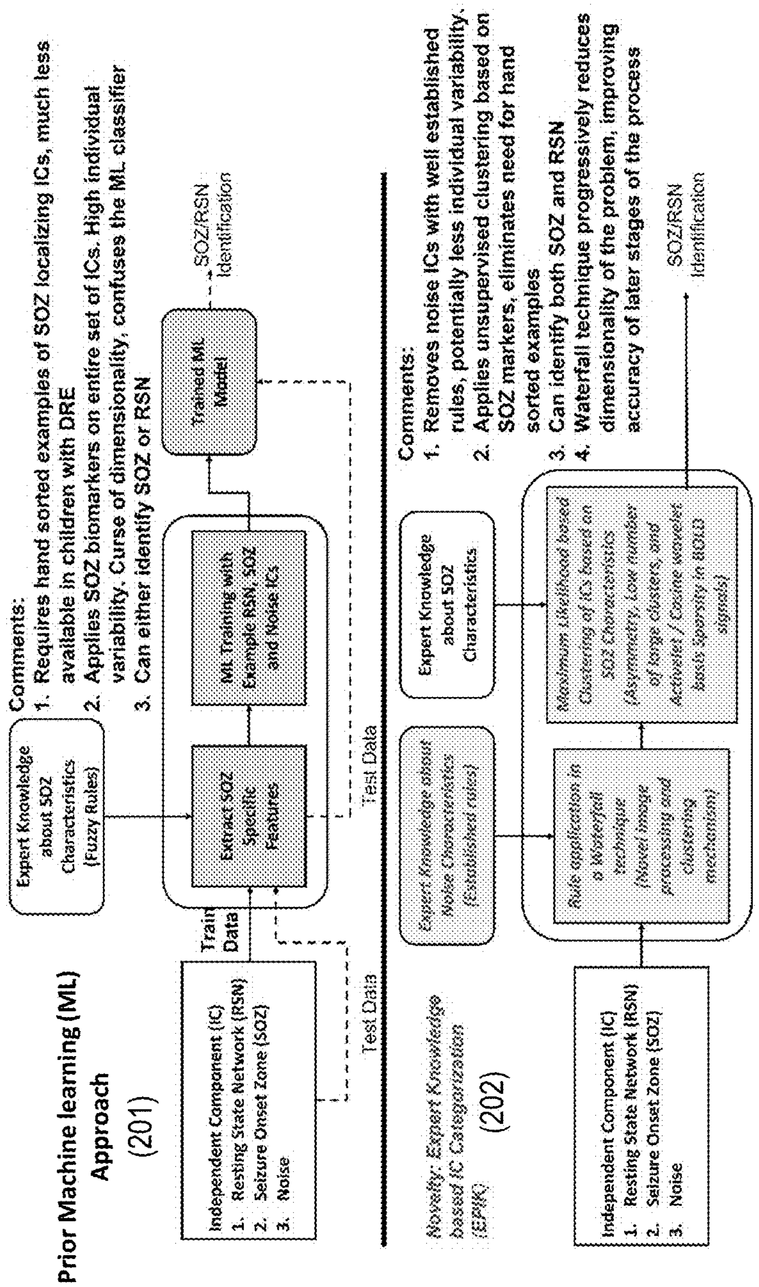
FIG. 2 is a flow diagram illustrating a comparison between other machine learning (ML) techniques and ML techniques associated with the inventive concept, EPIK, described herein.

Difference between EPIK and supervised ML: Referring to FIG. 2, a prior machine learning (ML) approach 201 is illustrated, along with a novel, unsupervised technique (EPIK) 202 is described to identify SOZ localizing ICs that requires no prior dataset for training and classifies ICs by encoding expert knowledge. The unsupervised nature of the associated algorithm of the present novel disclosure implies that the entire dataset is used as a test set and no training dataset is required. The algorithm is tested on the largest number of DRE children among the recent studies on automated SOZ identification mechanisms with rs-fMRI listed in Table 2. FIG. 2 illustrates differences from other techniques. Prior ML techniques and approaches (FIG. 2) utilize examples of SOZ and RSN ICs to learn a model in the training phase, which is subsequently used for identification of SOZ on previously unseen rs-fMRI signals. Such techniques have not been successful, possibly for the following reasons: 1) SOZ biomarkers are not precise and exhibit significant individual variance, and 2) patients have low number of SOZ localizing ICs as compared to noise and RSN, leading to imbalance in data and potential overfitting of ML models. Compared to prior ML techniques and approaches, EPIK first purges ICs with noise markers by employing rules compiled from experts. The ICs that pass the initial purge, are then classified into RSN and SOZ based on maximum likelihood-based clustering mechanism. The italicized text marks the innovation in this work.

In other words, EPIK (ExPert Knowledge based IC categorization) (FIG. 2) takes an alternative approach. Instead of directly learning SOZ related features from training data, EPIK first uses expert rules in a waterfall technique to purge noise ICs. Noise markers used by EPIK such as clusters outside brain boundaries or overlapping white matter or arteries, are well established, evidenced by consistency across several publications. It then uses SOZ specific spatial and temporal markers in a maximum likelihood-based clustering to further classify the ICs into RSN and SOZ. Clustering is unsupervised and does not implement training with prior data to tune its parameters.

To illustrate differences compared to prior ML approaches, we replicate shallow (Borbala Hunyadi, 2014) and implement a Convolution Neural Network (CNN) based DL technique for identification of SOZ localizing ICs from rs-fMRI thereby providing a preliminary comparative study of all three approaches on the same dataset of children with DRE using the standard metrics of accuracy, precision, specificity, and sensitivity. It is hypothesized that EPIK will perform at least equally well as prior methods and consistently across age and sex, due to being informed by developmental and sex informed expert sorting in the pediatric DRE population.

Materials and Methods

Inclusion Criteria:

Patients who were determined to be DRE by a treating epileptologist and received surgery evaluation. Most of the patients had focal epilepsy, however, rapid generalization of epileptiform activity from an epileptogenic focus may appear to be generalized epilepsy when evaluated using surface EEG. Hence generalized epilepsy was not an exclusion criterion.

Figure 3:
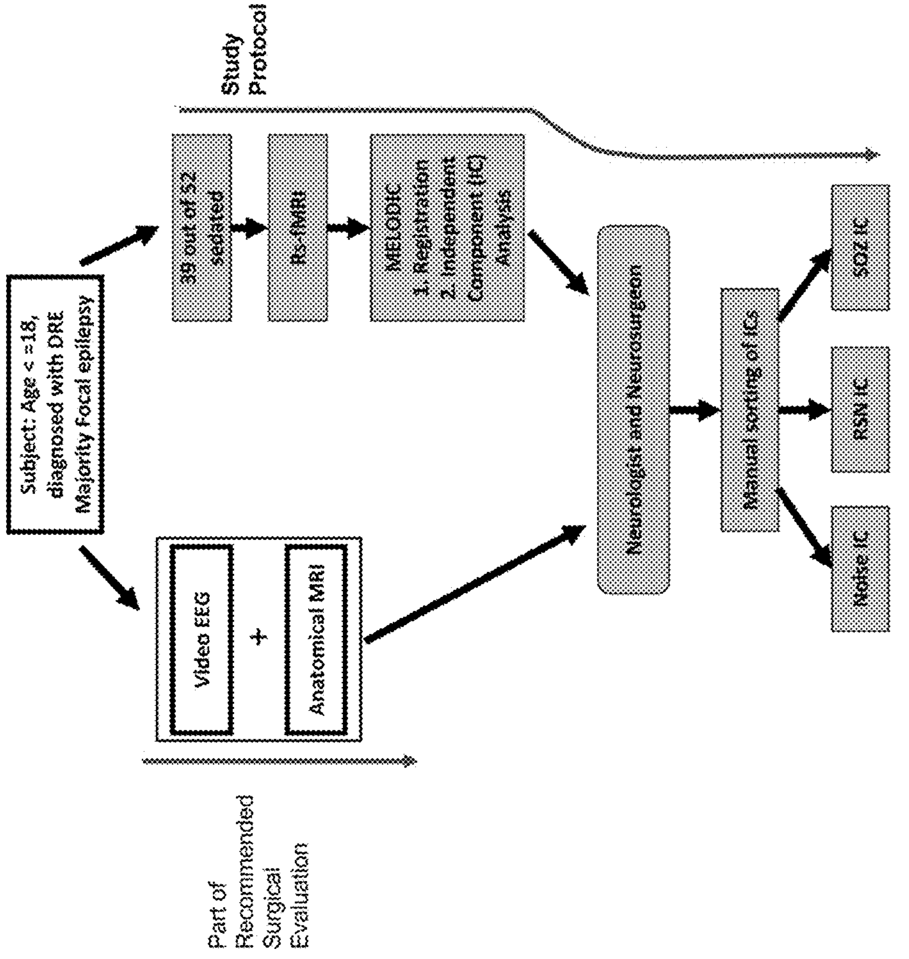
FIG. 3 is a flow diagram illustrating a study procedure for extracting noise, RSN and SOZ localizing ICs where subjects underwent video EEG and anatomical MRI as a part of the normal pre-surgical evaluation; in addition, the study protocol was also administered where rs-fMRI was collected.

Data Collection method: Referring to the flow diagram 300 of FIG. 3, the rs-fMRI data from 52 children with DRE, age 3 months-18 years old, were selected in descending alphabetical order from the PCH clinical database, who were under the care of a treating epileptologist at PCH. The diagnosis of DRE was according to the treating epileptologist's documented medical record notes. The children received rs-fMRI, video EEG, and anatomical MRI as part of standard clinical MRI SOZ localization for epilepsy surgery evaluation (FIG. 3). For rs-fMRI, patients who were determined to require conscious sedation received a propofol infusion, as a part of standard care determined by the institution's policies. In the 52 children, 39 required conscious sedation. The dataset included patients who had less than 1 mm head motion in any direction during scanning. For children who received sedation, propofol administered at levels to produce conscious sedation (80-110 micrograms/kilogram/minute), avoiding higher dosages typical of general anesthesia, was utilized. Propofol at levels producing conscious sedation reduces the BOLD signal strength by ~10%, still allowing for complete network detection. General anesthesia causes gross loss of ability to detect the large-scale cortical networks and, was, therefore avoided.

As part of standard of care the children also received inpatient video EEG and anatomical MRI. This data also aided the manual identification of SOZ localizing ICs in rs-fMRI (FIG. 3). The MRI images were acquired using a 3 T MRI unit, Ingenuity Philips Medical systems. It has 32 channel headcoil. The resting state fMRI parameters were set at TR 2000 ms, TE 30 ms, matrix size 80×80, flip angle 80°, number of slices 46, slice thickness 3.4 mm with no gap, in-plane resolution 3×3 mm, interleaved acquisition, and number of total volumes 600, in two 10 -min runs, with total time of 20 mins.

rs-fMRI pre-processing: Oxford Centre FMRIB (Functional MRI of the Brain) Software Library tool MELODIC, was used to analyze the rs-fMRI and extract ICs as detailed in. Pre-processing included deletion of the first 5 volumes to remove T1 saturation effects, passing through a high-pass filter at 100 seconds, slice time correction, spatial smoothing of 1-mm full-width at half maximum, and motion corrected by MCFLIRT, with nonbrain structures removed.

Linear registration was performed between the individual functional scans and patient's high-resolution anatomical scan which was further optimized using boundary-based registration. Individual rs-fMRI data sets then underwent independent component analysis (ICA) as previously reported.

Expert RS-fMRI evaluation methodology: The SOZ were evaluated by the expert epilepsy surgery conference team and deemed to be consistent with the other acquired data (video EEG and anatomical MRI) with high enough evidence to surgically target the SOZ. Further, the confirmation that the SOZ was deemed true by the treatment team as evidenced by the Engel I and II scores 1 year post-operatively.

The ICA results were viewed by two blinded reviewers (1 neurologist and 1 neurosurgeon) and sorted the ICs into 3 categories—noise, resting-state network, and rs-fMRI SOZ—by the criteria below. In case of disagreement between the first two reviewers, the opinion of a third reviewer (a neurologist) was used to make the final determination.

Rs-fMRI was categorized into noise, resting state network (RSN) and SOZ using the following criteria:

Noise category: Consistent noise markers in rs-fMRI are reported in various literature references. The noise markers reported in different manuscripts are summarized in Table 4.

RSN category: These are activations in the MRI images that are spatially located in established anatomical regions. Such regions are highlighted in literature references and include bilateral face area, bilateral leg area, and unilateral right- and left-hand regions, language networks, parietal networks, temporal networks, visual networks, default mode networks and the deep gray networks.

SOZ category: SOZ characteristics consist of two types of features: a) spatial features and b) temporal features.

Spatial features: The activation should, and in some examples must be located within the gray matter, while not overlapping with the RSN spatial patterns. It must have a bullseye pattern, where two or more overlapping abnormal neuronal IC can be identified. May have alternating activation and deactivation pattern that does not overlap noise zones shown in Table 4. May extend to ventricles through white matter. May have irregular borders.

Temporal features: The SOZ BOLD signal power spectra must contain dominant frequencies greater than 0.073 Hz, the rs-fMRI SOZ must have power spectra at higher frequencies than RSN, the BOLD time series may have irregular patterns.

The rs-fMRI IC were expert sorted and reported to the clinical epilepsy surgery evaluation team. The data includes ICs extracted using the MELODIC module in FSL. Table 3 shows the age and sex distribution and surgical outcome statistics.

TABLE 3

Patient distribution and information about the data set.

| Number of Subjects | 52 |
|---|---|
| Age <= 5 years | 20 |
| Age > 5 and <= 13 | 18 |
| Age > 13 and <= 18 | 14 |
| Male/Female | 23/29 |
| Prior surgery | 2 |
| Surgery Post Resting State fMRI | 24 (ablation 15, resection 7, disconnection 2) |
| Seizure Free post-surgery, and rs-fMRI SOZ is same location as region destroyed determined by expert review of pre-operative rs-fMRI SOZ and post-operative imaging | 16 (ablation 9, resection 6, disconnection 1) |

(Example) EPIK Method

Figure 4:
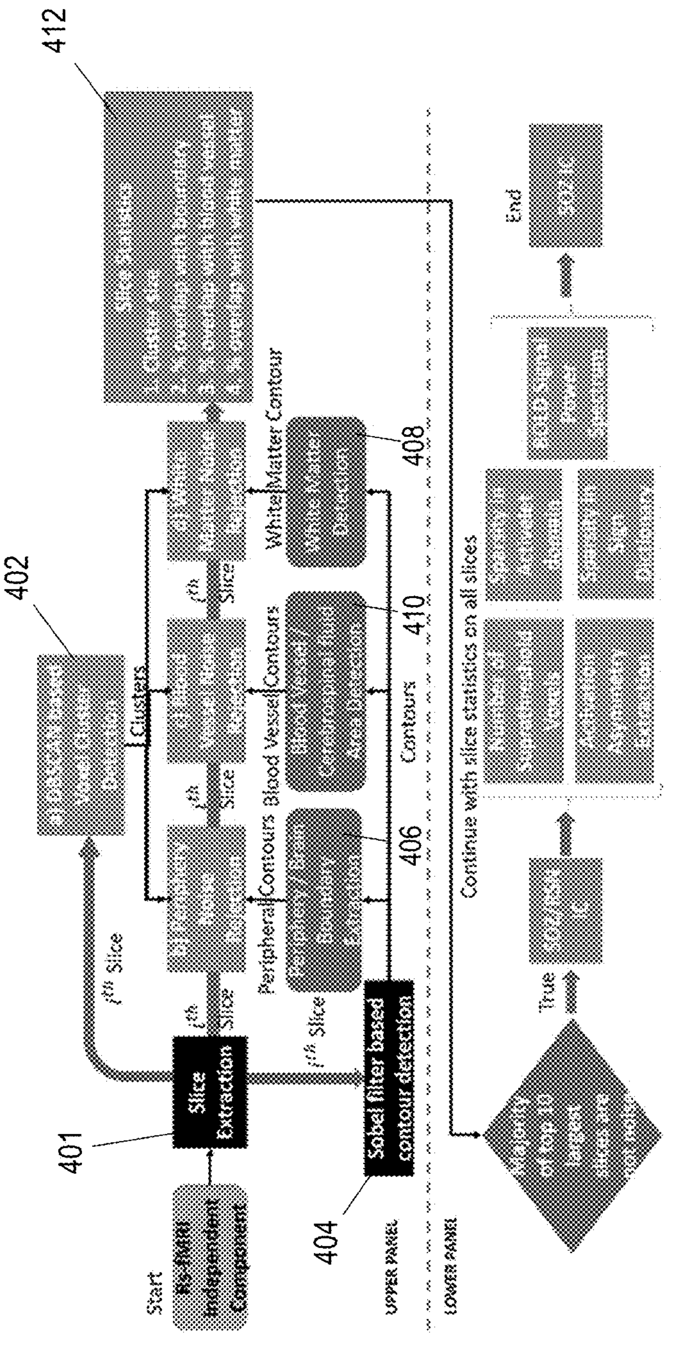
FIG. 4 is a flow diagram illustrating an unsupervised approach for SOZ classification.
Figure 5:
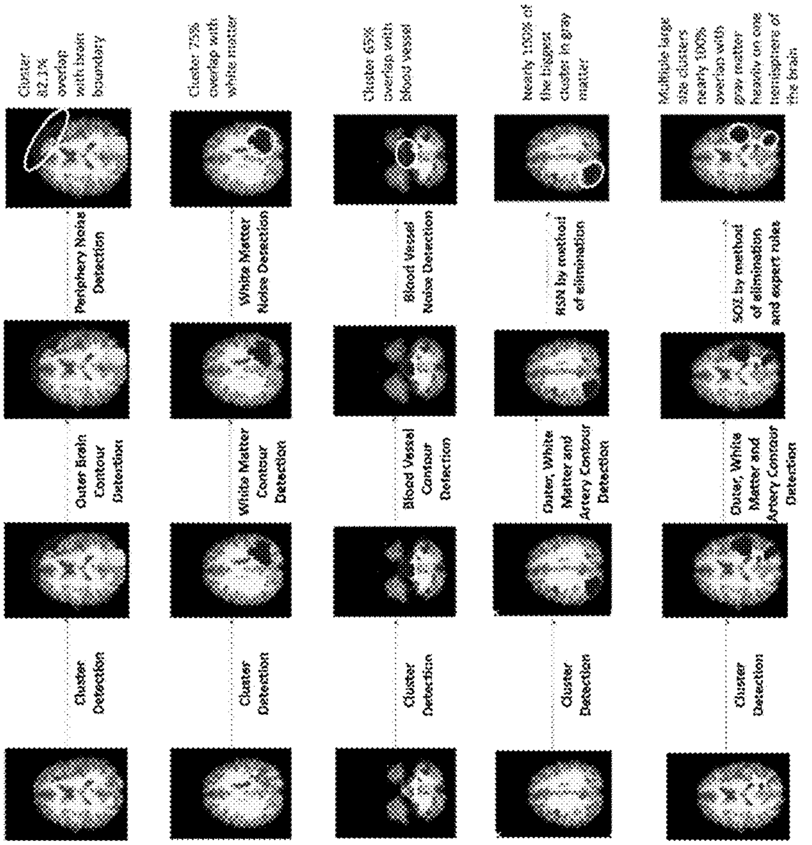
FIG. 5 is a series of images illustrating demonstration of an unsupervised IC sorting mechanism.

Referring to the sample method 400 of FIG. 4 illustrating the EPIK approach described herein, EPIK considers noise markers for ICs in an rs-fMRI as documented in several studies including Griffanti et al. The method 400 applies rules in a waterfall technique to classify an IC as noise (FIG. 4). If an IC is not noise, then it classifies the IC as either an RSN or a SOZ. In detail, examples can include six expert-derived rules for IC noise markers, combined from Boerwinkle and Hunyadi's works (Table 4), and other examples can include other expert-derived rules configurations/implementations. Automated application of such rules, necessitate the development of the following key components.

a) Voxel cluster detection algorithm (402): A density-based scanning approach is undertaken to derive voxel clusters (upper panel of FIG. 4). The algorithm 402 takes two configurable inputs: neighborhood, which includes a distance metric and a value ϵ, and minimum number of nearby voxels $v_{min}$. If a voxel has more than $v_{min}$ voxels in the ϵ neighborhood, then it is marked as a core point of a cluster. If a voxel is not a core point but is in ϵ neighborhood of a core point, then it is identified as border point. All other points are ignored from clusters. Core points, that are in ϵ neighborhood of each other, are combined into one cluster, and border points are assigned to the cluster of the nearest core point. The output of this step is the set of clusters in each IC slice (from slice extraction 401).

b) Brain boundary/periphery detection (406): Contours in the brain are derived using a Sobel filter-based edge detection technique (404 in FIG. 4). The lowest intensity contour is most likely the outer contour of the brain. However, the cerebrospinal fluid and blood vessels also present as low intensity contours. The method searches for the contour that encompasses all other contours, which gives us the brain periphery.

c) White matter detection (408): The white matter manifests as the brightest contour in the brain. The blood vessels and cerebrospinal fluid in the white matter contour are discarded.

d) Blood vessel detection (410*s*): The major basal-region blood vessels present themselves as low intensity contours encompassed in the brain periphery contour.

e) Noise IC classification: Utilizing the a,b,c, and d steps, an IC can be classified as noise (FIG. 5). From each slice of an IC, the clusters and the contours are extracted. An overlapping cluster can cause the contour detection algorithm to fail in extracting the peripheral, the white matter and the blood vessel contours. In the initial pass though the ICs, EPIK obtains a version of each slice devoid of clusters, which is subsequently used to identify contours. The algorithm then reruns through each slice of an IC and performs cluster detection. It then evaluates the overlap of the largest cluster with the brain boundary (first row of images 500 in FIG. 5), intersection of the largest cluster with the white matter, and blood vessels (third row in FIG. 5). The output of the first stage classifier (upper panel in FIG. 4) is a statistic for each slice on the cluster size, the percentage (%) overlap with the brain boundary, blood vessels, and white matter for each cluster in a slice (slice statistics 412 in FIG. 4).

Each IC has multiple slices (around 55 for PCH dataset). The second stage classifier sorts the slices in decreasing order of cluster size (lower panel of FIG. 2). It selects the top 10 slices and checks the % overlap to determine noise slices. If the majority of the top 10 slices are noise, the IC is classified as a noise IC. If the IC passes through the majority evaluation, it is passed to the second level classifier which determines if it is a normal RSN or an SOZ (FIG. 4). The SOZ classification is based on expert guidance on the SOZ markers in ICs as documented in Hunyadi et al (Table 4).

TABLE 4

| Noise markers in fMRI IC |
|---|
| Noise Independent Component (IC) Characteristics |
| 1. Large number of small voxel clusters |
| 2. Cluster peaks in white matter |
| 3. High overlap with white matter, cerebrospinal fluid or blood vessels |
| 4. Crescent shape aligning with the brain boundary |

TABLE 4-continued

| Noise markers in fMRI IC |
|---|
| Noise Independent Component (IC) Characteristics |
| 5. Sudden changes in the oscillation pattern in the BOLD signal |
| 6. Located within area of signal loss |

f) BOLD signal feature extraction: The BOLD signal was first divided into windows of length 256 samples. Four levels of activelet transformation coefficients using the 'a trois' algorithm with exponential-spline wavelets were extracted from each window. Sparsity in the activelet coefficients were evaluated using the Gini Index metric. A Gini Index of greater than 0.75 is sparse. If an IC is classified as white matter noise, then it can be classified as an SOZ if the Gini Index in the BOLD signal is greater than 0.75. In addition, sparsity in matching pursuit using sine dictionary limited to frequencies between 0.01 Hz to 0.1 Hz was also evaluated using the Gini index. If an IC was classified as white noise, then it can be classified as SOZ if the BOLD signal Gini Index in the sine dictionary matching pursuit is greater than 1.72.

Likelihood-Based Classification for SOZ ICs

The main aim of the likelihood-based classification step is a standard technique in ML. We want to obtain a 1×4 weight vector ω, such that $ex_i \cdot \omega = \rho_i$ corresponds to the likelihood that the largest cluster in IC i is the SOZ. To obtain such a weight vector we solve the following optimization problem:

Given: A set Ex of expert knowledge-based representations (g_i={KNumC, KThruV, KDomF, KSparseF}) of a sample of RSN and SOZ ICs and a set $y_i \in C$ of one hot encodings of two classes, such that $y_i=-1$ if $i \in Ex$ is RSN and $y_i=1$ if $i \in Ex$ is SOZ.\\

Find: A 4×1 weight vector ω that

Minimizes:

$$P\sum_{i=1}^{|Ex|}(1-y_i ex\cdot\omega)^2$$

Such that:

$$\sum_1^4 \omega_k = 1,$$

where P is a penalty factor. The constraint in the problem formulation ensures that the confidence score is solely and exclusively based on the expert knowledge, and $\omega_k$ $ex_k$ is the contribution of the k-th knowledge component. This contribution factor $\omega_k$ $ex_k$ is later used for generating explanations.

It should be understood that the above weight configurations are merely exemplary, and the inventive concept can include other weight amounts; i.e., other classifier configurations are contemplated. In addition, the classifier as described can be one of one or more machine learning approaches implemented as part of an artificial intelligence mode (AI model). As such, other AI approaches including different machine learning models may be implemented for identification of SOZ ICs.

DL Strategy for SOZ Localization

Nozais et al. recently proposed a DL based technique where a multi-layer perceptron (MLP) is trained on 12690

RSNs from 282 participants. As such, it does not incorporate any expert knowledge but instead attempts to build its own hypothesis from examples. The technique has not been used to classify SOZ and can currently only identify RSNs. We have implemented CNN based DL for SOZ localization.

For the CNN technique, hyperparameter tuning is one of the most important steps. A Keras-Tuner was implemented to get the optimal values of the hyperparameters. We used hyperband algorithm with the objective of least validation loss to select the best model of CNN by optimizing the following hyperparameters:

Number of layers: [3; 4; 5]

Number of units/filters per layer: min_value=32, max_value=512, default=128.

Learning rate: [$10^{-2}$, $10^{-3}$; $10^{-4}$]

Dropout rate: [0; 0.2; 0.33; 0.4; 0.5; 0.66].

4212 ICs were used for training and 1404 ICs were used for validation in the hyperparameter tuning process. The input shape of the IC image was down sampled from 1006×709×3 to 270×400×3 during preprocessing. Binary cross-entropy was used as a loss function and Adam was used as an optimizer. To avoid the overfitting problem, "dropout" and "early_stopping" strategies were implemented. "ReLU" being more computationally efficient was used as an activation function for the input and hidden layers, and "Sigmoid" activation function was used for the output layer. For CNN, weights were initialized using "He uniform" initializer.

Shallow Learning Strategy

The technique proposed in Hunyadi et al. was replicated. rs-fMRI image and BOLD signal features were extracted from the IC images. 60% of the data from the entire pool of ICs was randomly sampled to be used as training data. The remaining 40% was used for testing. The features extracted from the rs-fMRI image and BOLD signal was used to train a Least Squares Support Vector Machine (LS-SVM) as described in Hunyadi et al.

Metrics and Statistical Analysis Method

We evaluated performance of each approach for two objectives: a) noise IC removal, and b) SOZ localizing IC identification. For the first objective, we define true positives (TP) as ICs that are classified as RSN or SOZ by both expert and the automated approach, true negatives (TN) as ICs that are classified as noise by both expert and the automated approach, false positives (FP) as ICs classified as noise by expert but RSN or SOZ by automated approach, and false negatives (FN) as ICs classified as RSN or SOZ by expert but noise by automated approach. For the second objective we define TP as ICs classified by both expert and automated approach as SOZ, TN as ICs classified by both expert and automated approach as not SOZ, FP as ICs classified as non-SOZ by expert but SOZ by automated approach, and FN as ICs classified as SOZ by expert but non SOZ by automated approach. From these we derived accuracy, precision, sensitivity, and specificity.

We evaluated the statistical significance of a difference in performance metrics between two approaches by utilizing a one-sided paired t test. The alternate hypothesis was that there is a positive non-zero difference between EPIK and any other approach (LS-SVM or CNN). The alternate hypothesis was rejected if the p-value for the paired t test was less than 0.05.

We also evaluated the effect of age and gender on each approach using a mixed effects model with each parameter as the observation variable and age or gender as the predictor variable. A random effect on the patient ID was also introduced. For each algorithm, a separate mixed effects model was generated for each metric and for each predictor variable age/gender.

Overall Identification Results

We compared performance of EPIK with two competing ML based approaches: shallow learning (LS-SVM) and deep learning (CNN). For the ML based approach, training data was used from every subject. This is also known as user-dependent supervised classification approach and gave us the best performance metrics. For EPIK no such training set is needed. The results in Table 5 show that EPIK outperforms both LS-SVM and CNN approaches for SOZ localizing IC identification task. The CNN approach is more accurate in noise removal, however, performs poorly in the SOZ identification task.

EPIK has high sensitivity in the SOZ identification task with low number of FNs. This implies that EPIK rarely misses any SOZ localizing IC. The LS-SVM approach is poor in noise removal, but its performance improves for the SOZ identification task. The confidence interval is specified as [a,b] for metrics with p<0.5.

TABLE 5

Overall RSN or SOZ identification results for the three approaches.

| | RSN or SOZ v.s. Noise | | | | SOZ v.s. Non SOZ (RSN or noise) | | | | Key |
|---|---|---|---|---|---|---|---|---|---|
| Approach | Accuracy | Precision | Sensitivity | Specificity | Accuracy | Precision | Sensitivity | Specificity | Observations |
| EPIK (Banerjee et al) | 71.7% | 73.1% | 72% | 73.7% | 84.7% | 74.1% | 88.6% | 81.9% | Best performance for SOZ identification |
| LS-SVM (Hunyadi et al) | 61.8% | 52.2% | 43% | 73.6% | 80.7% | 52.2% | 72.1% | 78.7% | High false positives and false negatives |
| One sided t test for +ve difference between EPIK and LS-SVM | p value = ~0 [5, 15.2] | p value = ~0 [18.7, 27.4] | p value = ~0 [27.4, 45.9] | Rejected p value = 0.9 | p value = ~0 [2, 6.5] | p value = ~0 [20.7, 29.1] | p value = ~0 [14.1 25.3] | Rejected p value = 0.06 | Significant variance across patients |

TABLE 5-continued

Overall RSN or SOZ identification results for the three approaches.

| Approach | RSN or SOZ v.s. Noise | | | | SOZ v.s. Non SOZ (RSN or noise) | | | | Key |
|---|---|---|---|---|---|---|---|---|---|
| | Accuracy | Precision | Sensitivity | Specificity | Accuracy | Precision | Sensitivity | Specificity | Observations |
| CNN (Nozais et al) | 82.45% | 82.7% | 82.1% | 81.5% | 73.5% | 28.5% | 97.7% | 42.85% | Best RSN identification performance. |
| One sided t test for +ve difference Between EPIK and CNN | Negative change P value ~0 [−5.1, −13.2] | Rejected P value = 0.6 | Negative change P value ~0 [−7, −12.1] | Negative change P value = 0.02 [−4.1, −9] | P value ~0 [8.3, 15.7] | P value ~0 [51.2, 60] | Negative change P value ~0 [−4.2, −11.3] | P value = 0.001 [31.6 45.2] | Poor SOZ performance due to lack of hand sorted SOZ IC examples. |
| EPIK (Banerjee et al) | 71.7% | 73.1% | 72% | 73.7% | 84.7% | 74.1% | 88.6% | 81.9% | Best performance for SOZ identification |
| LS-SVM (Hunyadi et al) | 61.8% | 52.2% | 43% | 73.6% | 80.7% | 52.2% | 72.1% | 78.7% | High false positives and false negatives |
| One sided t test for +ve difference between EPIK and LS-SVM | p value = ~0 [5, 15.2] | p value = ~0 [18.7, 27.4] | p value = ~0 [27.4, 45.9] | Rejected p value = 0.9 | p value = ~0 [2, 6.5] | p value = ~0 [20.7, 29.1] | p value = ~0 [14.1 25.3] | Rejected p value = 0.06 | Significant variance across patients |
| CNN (Nozais et al) | 82.45% | 82.7% | 82.1% | 81.5% | 73.5% | 28.5% | 97.7% | 42.85% | Best RSN identification performance. |
| One sided t test for +ve difference Between EPIK and CNN | Negative change P value ~0 [−5.1, −13.2] | Rejected P value = 0.6 | Negative change P value ~0 [−7, −12.1] | Negative change P value = 0.02 [−4.1, −9] | P value ~0 [8.3, 15.7] | P value ~0 [51.2, 60] | Negative change P value ~0 [−4.2, −11.3] | P value = 0.001 [31.6 45.2] | Poor SOZ performance due to lack of hand sorted SOZ IC examples. |

Performance Variation with Age and Gender

Table 6 shows the variation of the performance metrics for EPIK, LS-SVM and CNN with respect to age and gender. The accuracy, precision, and sensitivity of EPIK for noise removal does not have a statistically stable dependence on age or gender. The specificity of EPIK for noise removal decreases with age resulting in more FPs, where noise is categorized as RSN or SOZ. For the SOZ identification task, there is a statistically significant trend for sensitivity to increase and specificity to decrease with age. This implies that as age progresses EPIK tends to classify more RSN or noise as SOZ, however, less SOZs are ignored as noise. Consequently, EPIK is observed to have accuracy greater than 85% at ages below 5, which is higher than those previously reported.

The LS-SVM approach had consistently better performance for SOZ identification task than noise removal. It also had the same pattern of increasing sensitivity and decreasing specificity with age. The LS-SVM approach had higher variance in performance across subjects. This indicates that the hand-crafted features chosen in Hunyadi et al. may be less applicable to specific scenarios of DRE in children.

TABLE 6

Age and Sex segregated metrics for unsupervised IC classification algorithm, LS-SVM approach by Hunyadi et al, and CNN deep learning approach.

| | Metric | | | | | | | | |
|---|---|---|---|---|---|---|---|---|---|
| | Algorithm | 0 < Age ≤ 5 (N = 20) | 5 < Age ≤ 13 (N = 18) | 13 < Age ≤ 18 (N = 14) | P value Fixed effects on Age | Male (N = 23) | Female (N = 29) | P value Fixed effects on Sex | Key Observations |
| Noise v.s. Network/SOZ performance metrics | | | | | | | | | |
| Accuracy | EPIK | 69.4% (±9%) | 74% (±8.2%) | 71.7% (±5.8%) | 0.32 | 73.8% (±5.3%) | 70% (±9.4%) | 0.04$^{\dagger}$ | 1. CNN gives best RSN |
| | LS-SVM | 55.8% (±11.5%) | 63.7% (±7.7%) | 65.3% (±8.4%) | 0.004$^{\dagger}$ | 63.6% (±9.5%) | 59.1% (±10.6%) | 0.06 | identification accuracy for |
| | CNN | 73.2% (±4.5%) | 76.1% (±0.6%) | 80.2% (±5.8%) | ~0 | 72.8% (±8.2%) | 77.4% (±4.7%) | 0.09 | all age categories. |

TABLE 6-continued

Age and Sex segregated metrics for unsupervised IC classification algorithm, LS-SVM approach by Hunyadi et al, and CNN deep learning approach.

| | | Metric | | | | | | | |
|---|---|---|---|---|---|---|---|---|---|
| | Algorithm | 0 < Age ≤ 5 (N = 20) | 5 < Age ≤ 13 (N = 18) | 13 < Age ≤ 18 (N = 14) | P value Fixed effects on Age | Male (N = 23) | Female (N = 29) | P value Fixed effects on Sex | Key Observations |
| Precision | EPIK | 74.9% (±16.2%) | 73.6% (±13.7%) | 66.5% (±10%) | 0.048 | 73.5% (±11.5%) | 71.1% (±16%) | 0.27 | followed closely by |
| | LS-SVM | 55.6% (±32.4%) | 52.8% (±15.9%) | 46.5% (±18%) | 0.3 | 54.8% (±22.2%) | 50.1% (±25.4%) | 0.24 | EPIK 2. LS-SVM is |
| | CNN | 68.2% (±11.7%) | 75.2% (±1.5%) | 75.4% (±7.3%) | ~0 | 69.2% (±13%) | 75.91% (±15.1%) | 0.3 | poorest in identifying |
| Sensitivity | EPIK | 63% (±18%) | 76.6% (±9.3%) | 76.8% (±9.7%) | 0.001† | 75.2% (±10.7%) | 68.43% (±16.9%) | 0.047 | RSN since it only considers |
| | LS-SVM | 27.5% (±25.9%) | 50.8% (±26.9%) | 55.1% (±22%) | 0.001† | 52.6% (±28.9%) | 35.4% (±24.9%) | 0.012† | SOZ markers in ICs. |
| | CNN | 86.09% | 81.5% | 85.96% | | 78% | 79.5% | | 3. Success of |
| Specificity | EPIK | 79% (±13.8%) | 72.7% (±17.1%) | 68.2% (±8.4%) | 0.01† | 73.4% (±13.5%) | 74.2% (±15.2%) | 0.41 | CNN can be attributed to |
| | LS-SVM | 80.5% (±17.4%) | 68.8% (±23%) | 70% (±10%) | 0.035† | 71.3% (±17%) | 75.5% (±19.9%) | 0.2 | availability of a significant |
| | CNN | 60.5% | 70.8% | 75% | | 67.9% | 75.31% | | number of normal RSN ICs (n = 2427) |
| | | SOZ Identification Metrics | | | | | | | |
| Accuracy | EPIK | 87.5% (±7.6%) | 83.5% (±9.6%) | 82.2% (±6.1%) | 0.025† | 84.6% (±6.7%) | 84.7% (±9.3%) | 0.48 | 1. EPIK has the best |
| | LS-SVM | 85.3% (±6.6%) | 77.2% (±9.4%) | 78.6% (5.7%) | 0.008† | 79.5% (±8.8%) | 81.6% (±7.7%) | 0.17 | performance for SOZ |
| | CNN | 75.5% (±27.7%) | 75.3% (±26.6%) | 76.5% (±21%) | 0.8 | 71% (±28.2%) | 73% (±30.2%) | 0.44 | localizing IC identification |
| Precision | EPIK | 76.7% (±16.3%) | 75.2% (±14.4%) | 69.2% (±9.9%) | 0.07 | 76.3% (±10.7%) | 72.5% (±16.5%) | 0.17 | 2. EPIK has consistent |
| | LS-SVM | 62.5% (±17.2%) | 56.9% (±15%) | 51.4% (±15%) | 0.06 | 54.7% (±15.7%) | 55% (±16.3%) | 0.2 | performance across age. |
| | CNN | 53.8% (±50.2%) | 50% (±51.4%) | 45% (±50%) | 0.035 | 45.9% (±49.9%) | 54.4% (±50%) | 0.54 | 3. EPIC has the best |
| Sensitivity | EPIK | 86.8% (±8.8%) | 89.4% (±6.8%) | 90.4% (±7.6%) | 0.085† | 88.1% (±7.1%) | 89.1% (±8.5%) | 0.34 | performance for children of |
| | LS-SVM | 58.8% (±33.9%) | 74.6% (±19.5%) | 87.8% (±23%) | 0.001† | 78.83% (±25.6%) | 66.7% (±30.4%) | 0.065 | age less than 5 years. This |
| | CNN | 11.1% (±3%) | 0 (±0) | 0 (±0) | 0.001 | 20% (±5%) | 3.44% (±3%) | 0.002 | is a key benefit because it is |
| Specificity | EPIK | 86.6% (±12.8%) | 79.9% (±15.6%) | 77.8% (±8%) | 0.02† | 81.7% (±12.1%) | 82% (±14.2%) | 0.47 | known that earliersurgery |
| | LS-SVM | 86.4% (±14.1%) | 73.2% (±21.8%) | 74.9% (±9.3%) | 0.015† | 75.3% (±17%) | 81.5% (±17%) | 0.09 | for epilepsy yields better |
| | CNN | 74.9% (±27.6%) | 75.3% (±26.6%) | 76.1% (±22%) | 0.4 | 75.37% (±28.2%) | 76.59% (±30%) | 0.8 | surgical and developmental outcomes. |

†Indicates that the result has a p value of less than 0.05 and is statistically significant.

CNN approach outperformed EPIK and LS-SVM for all age groups for noise removal. However, it had lower performance for SOZ identification. In the training data there were only 318 SOZ localizing ICs as opposed to 2427 RSN IC. This may have led to underfitting of CNN technique for SOZ identification. For CNN technique in noise removal, both sensitivity and specificity increased with age. This potentially indicates that CNN technique is finding novel hidden features from the ICs that are characteristic of RSN but not SOZ.

Overall, EPIK provided consistent performance across the three age categories considered in this study compared to prior reported methods. Whereas the ML techniques of Hunyadi and CNN have significantly higher variance, possibly indicating inconsistent performance.

Performance on Subjects Undergoing Surgery

Out of the 52 subjects considered in this study 24 underwent surgery. The surgical outcomes were varied with 16 becoming seizure free (Engel I) after surgically destroying expert identified SOZ using rs-fMRI and 7 having reduced post operative seizure frequency (Engel II) (Table 7). We focused on EPIK and LS-SVM for the SOZ identification task on the 24 subjects that underwent surgery, because CNN had significantly poorer performance than the other two.

Figure 6:
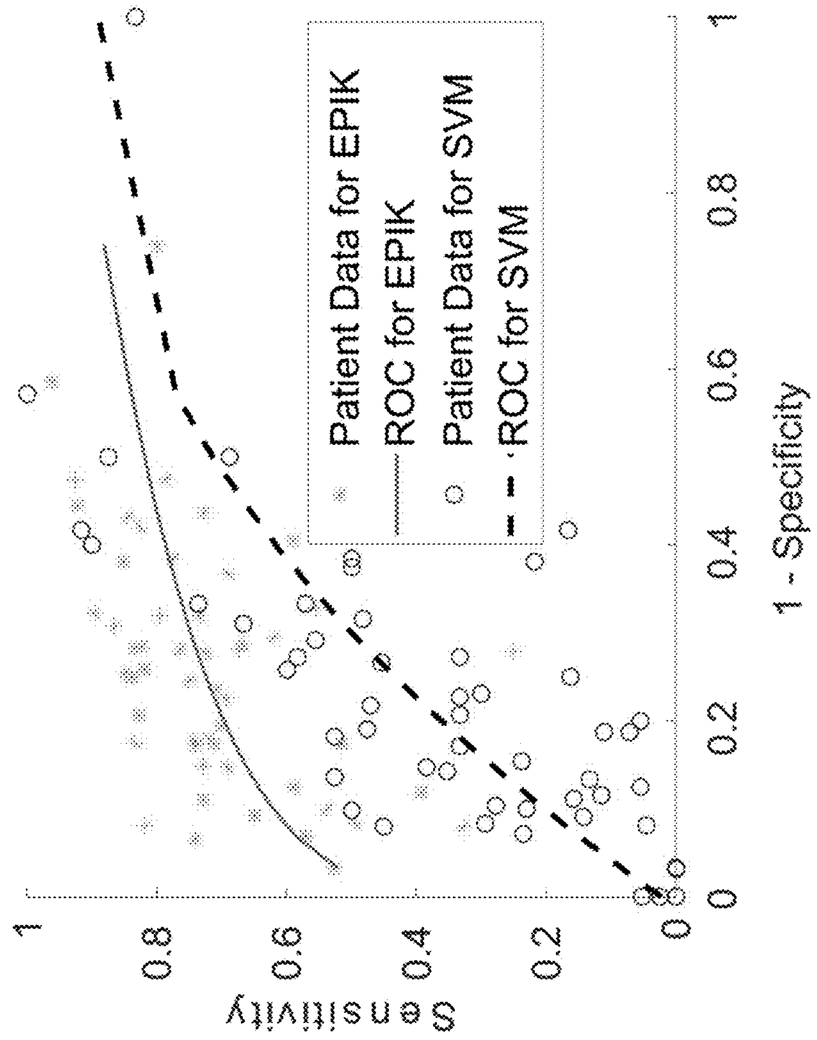
FIG. 6 is a graph illustrating receiver operating characteristics (ROC) curve for EPIK and LS-SVM approaches for patients undergoing surgery.

Table 7 shows that, for subjects whose post operative outcomes are either seizure free or significantly reduced frequency, the agreement between EPIK and expert hand classification is significantly high (88.9% sensitivity and 79% specificity). Although LS-SVM approach has nearly similar accuracy as EPIK, Sensitivity is far lower in LS-SVM, with significant individual variance. To better understand the difference between EPIK and LS-SVM approach, the graph 600 of FIG. 6 shows the receiver operating characteristics (ROC) curve for both EPIK and LS-SVM. EPIK exhibits higher sensitivity and specificity than LS-SVM, which appears to possibly sacrifice one for the other. More specifically, FIG. 6 shows an ROC curve for EPIK and LS-SVM approach for patients undergoing surgery. A curve close to the top left-hand corner of the graph is favorable and shows a balance between sensitivity and specificity.

For patients undergoing ablation surgery the specificity for EPIK was 82.9% while the sensitivity was 88%. This is preliminarily encouraging result given that ablation is minimally invasive and thus largely accepted as less risky than resection. The specificity and sensitivity in EPIK for patients undergoing resection reduces to 79.5% and 86.6% respectively. Ten out of 15 subjects with ablation procedure were seizure free (Engel 1 outcome), which is slightly better than recently reported statistics (66% in this study, versus. 60.4% reported in other studies).

TABLE 7

Performance of EPIK and LS-SVM approaches for subjects undergoing surgery. The table also shows the difference in agreement between automated approach and expert hand classification for subjects with seizure free/reduced frequency post operative outcome and without any change in seizure frequency.

| Age Years (months) | Sex | Pre-Surgery frequency (per month) | Post-Surgery Frequency (per month) | Procedure | Method | Accuracy | Precision | Sensitivity | Specificity |
|---|---|---|---|---|---|---|---|---|---|
| 18 | F | 1 | 0 | A | EPIK | 82.8% | 71.7% | 82.5% | 82.9% |
| (0) | | | | | LS-SVM | 78.7% | 58.8% | 76.9% | 79.4% |
| 14 | M | 1 | 0 | A | EPIK | 85.2% | 75.5% | 90.2% | 82.1% |
| (8) | | | | | LS-SVM | 68.2% | 48% | 92.3% | 58.1% |
| 14 | F | 3 | 1 (66% | A | EPIK | 86.5% | 78.2% | 95.6% | 79.7% |
| (7) | | | reduced) | | LS-SVM | 71.4% | 52% | 100% | 58.6% |
| 14 | M | 1 | 0 | A | EPIK | 86.3% | 77.1% | 86.1% | 86.4% |
| (10) | | | | | LS-SVM | 82% | 35.7% | 100% | 80% |
| 16 | F | 210 | 0 | A | EPIK | 86.5% | 67.9% | 97.4% | 82.4% |
| (3) | | | | | LS-SVM | 91.3% | 37.5% | 100% | 63.5% |
| 10 | F | 240 | 0 | A | EPIK | 74.2% | 60.5% | 95.8% | 60.5% |
| (1) | | | | | LS-SVM | 76% | 60% | 100% | 62.5% |
| 8 | M | 4 | 2 (50% | A | EPIK | 83.3% | 77% | 94.1% | 73.1% |
| (2) | | | reduced) | | LS-SVM | 85.4% | 71.4% | 83.3% | 86.2% |
| 15 | F | 12 | 0 | A | EPIK | 86% | 62.9% | 78.6% | 88% |
| (6) | | | | | LS-SVM | 87.3% | 0 | 0 | 97.9% |
| 10 | F | 60 | 8 (87% | A | EPIK | 85.5% | 69.6% | 91.4% | 82.9% |
| (5) | | | reduced) | | LS-SVM | 83% | 40% | 66.7% | 85.4% |
| 3 | F | 60 | 1 (98% | A | EPIK | 87.4% | 78% | 86.5% | 87.8% |
| (2) | | | reduced) | | LS-SVM | 88.9% | 81.8% | 75% | 94% |
| 17 | M | 2 | 0 | A | EPIK | 74.3% | 50% | 88.9% | 69.2% |
| (9) | | | | | LS-SVM | 75% | 25% | 66.7% | 76% |
| 11 | M | 1 | 0 | R | EPIK | 80.6% | 62.5% | 65.8% | 85.8% |
| (8) | | | | | LS-SVM | 82.8% | 16.7% | 16.7% | 90.4% |
| 4 | F | 2 | 0 | R | EPIK | 84.1% | 72.7% | 84.2% | 84% |
| (9) | | | | | LS-SVM | 80.4% | 14.3% | 25% | 85.7% |
| 18 | F | 5 | 0 | R | EPIK | 72% | 55.6% | 87% | 64.4% |
| (1) | | | | | LS-SVM | 71.4% | 50% | 75% | 70% |
| 10 | F | 8 | 0 | R | EPIK | 57.5% | 44.1% | 93.8% | 38.7% |
| (5) | | | | | LS-SVM | 63.1% | 58.8% | 100% | 22% |
| 13 | M | 120 | 1 (99% | R | EPIK | 82.9% | 72.9% | 93.5% | 75.4% |
| (8) | | | reduced) | | LS-SVM | 77.8% | 43.7% | 87.5% | 75.7% |
| 2 | F | 2 | 0 | D | EPIK | 84.5% | 53.2% | 100% | 81.3% |
| (7) | | | | | LS-SVM | 81.8% | 38.5% | 100% | 79.5% |
| 2 | M | 720 | 0 | A | EPIK | 89.1% | 81.3% | 88.6% | 89.3% |
| (7) | | | | | LS-SVM | 90.4% | 50% | 60% | 93.6% |

TABLE 7-continued

Performance of EPIK and LS-SVM approaches for subjects undergoing surgery. The table also shows the difference in agreement between automated approach and expert hand classification for subjects with seizure free/reduced frequency post operative outcome and without any change in seizure frequency.

| | | | | | | | | | |
|---|---|---|---|---|---|---|---|---|---|
| 0 | F | 90 | 30 (66% | A | EPIK | 98.8% | 100% | 92.9% | 100% |
| (3) | | | reduced) | | LS-SVM | 97.1% | 100% | 50% | 100% |
| 2 | F | 300 | 0 | R | EPIK | 84.8% | 74.5% | 97.4% | 75.5% |
| (10) | | | | | LS-SVM | 89.2% | 71.4% | 100% | 85.2% |
| 2 | M | 4 | 0 | D | EPIK | 69.1% | 61% | 96.2% | 44.8% |
| (11) | | | | | LS-SVM | 81.8% | 78.9% | 100% | 42.8% |
| 2 | F | 3000 | 0 | A | EPIK | 88.4% | 45% | 60% | 91.6% |
| (1) | | | | | LS-SVM | 88.1% | 25% | 20% | 94.4% |
| 3 | M | 30 | 0 | A | EPIK | 88.6% | 78.6% | 91.7% | 87% |
| (6) | | | | | LS-SVM | 78.6% | 68.4% | 100% | 60% |
| 1 | F | 180 | 0 | R | EPIK | 94.1% | 94.3% | 84.6% | 98% |
| (4) | | | | | LS-SVM | 88.9% | 50% | 16.7% | 98% |

| Approach | Mean Accuracy (SD) | Mean Precision (SD) | Mean Sensitivity (SD) | Mean Specificity (SD) |
|---|---|---|---|---|
| Agreement with expert hand classification for seizure free/reduced post operative outcome | | | | |
| EPIK | 83.3% (8.43%) | 69.45% (13.6%) | 88.9% (9.6%) | 79% (14.4%) |
| LS-SVM | 80.45% (9.8%) | 47.6% (23.9%) | 72.5% (32.6%) | 75.5% (19.5%) |
| Agreement with expert hand classification for Ablation Procedures | | | | |
| EPIK | 85.5% (5.8%) | 71.6% (13.4%) | 88% (9.3%) | 82.9% (9.6%) |
| LS-SVM | 82.8% (8.1%) | 50.2% (24.9%) | 72.7% (30.5%) | 79.3% (15.3%) |
| Agreement with expert hand classification for Resection Procedures | | | | |
| EPIK | 79.4% (11.6%) | 68.1% (16%) | 86.6% (10.5%) | 74.5% (18.9%) |
| LS-SVM | 79.1% (9.4%) | 43.6% (21.1%) | 60.1% (39.1%) | 75.3% (25.2%) |

*A—Ablation, R—Resection, D—Disconnection

Reduction in IC Sorting Effort for the Neurosurgeon/Neurologist

The ICs marked as SOZ by the EPIK method can be supplied to the Neurosurgeon or neurologist for localization of SOZs in the brain. The number of SOZ classifications in EPIK per subject is 22 (±4). Out of which 16 are true positive SOZ ICs, 2 are noise ICs, and 4 are RSN ICs. These ICs are then evaluated by the neurosurgeon or neurologist for determining SOZ in the brain. This implies that there is ~5 times reduction in the number of ICs to be analyzed by the neurosurgeon or neurologist. This can significantly aide in pre surgical screening by reducing the cognitive burden of the neurosurgeon or neurologist and improve accuracy of the SOZ identification.

Discussion

A strength of EPIK, that may increase its utility, is that it does not require any prior training data and hence it is a plug-n-play IC sorting method. EPIK combines spatial and temporal markers specific for RSN and SOZ which results in possibly equivalent or better performance than prior methods. The waterfall technique removes the number of noise ICs using well established expert rules, hence may reduce false positives and increase true positives of SOZ localizing ICs.

For subjects with good post operative outcomes, there was excellent agreement between expert hand sorting and EPIK based SOZ localizing IC identification. Also, EPIK appeared to performance well in those less than 5 years of age, in whom surgery yields improved developmental outcomes.

The LS-SVM approach did not performs as well for the noise identification task, but drastically improves for SOZ identification task. This was expected because the hand selected features proposed by Hunyadi et al. are specifically geared towards the SOZ identification task. However, LS-SVM exhibits significant valiance in performance across subjects resulting in inconsistent accuracy in this study. EPIK had higher and consistent balance in identification of all three categories of IC compared to LS-SVM herein.

The CNN approach had the lower performance for SOZ identification. However, there was a significant improvement in the performance for the noise identification task. This can be explained by the difference in data availability for the two tasks. This gives confidence that CNN can perform better if given adequate number of training-SOZ-localizing ICs, an avenue for future research.

Additional Directions

Subtypes of epilepsy-acquired, congenital/genetic, and surgical approaches success metrics should be statistically evaluated with acceptable power. Lastly, repeat studies in same individuals over time would increase knowledge of validity and reproducibility of the tool.

The majority of the subjects in this study received propofol infusion for sedation as part of standard of clinical care for epilepsy surgery evaluation. Head motion maximum was less than 1 mm framewise displacement in any direction. Although propofol use has minimal effect on the overall rs-fMRI BOLD signal, it puts small but additional risks on the child. Several research works have proposed alternate methods of reducing head motion, through engaging the child with videos and post processing by measuring and accounting for head movements through computational methods. An area of future study is to evaluate the effect of sedation on the EPIK SOZ identification accuracy and integration of live motion monitoring and reduction-based approaches towards elimination of head movement artifacts.

General Non-Limiting Conclusions

1. EPIK identified seizure onset zone (SOZ) localizing resting state fMRI independent components in children with drug resistant epilepsy with accuracy of 84.7% in this preliminary study.
2. EPIK can reduce the number of potential ICs to be analyzed by the neurosurgeon by ~5-fold, hence significantly reducing the time commitment for pre-surgical evaluation.
3. EPIK is unsupervised and does not need any prior example of SOZ and works by codifying expert knowledge about fMRI noise and SOZ markers.
4. EPIK had consistent performance across age groups, gender, and has been validated with surgical outcomes.
5. EPIK appeared to performance best for those under 5 years of age, and thus may enable successful surgeries early in their life, potentially improving long-term post operative outcomes.
6. EPIK preliminary performed as well or better than shallow and deep learning systems for identification of SOZ localizing ICs in resting state fMRI.

Figure 7:
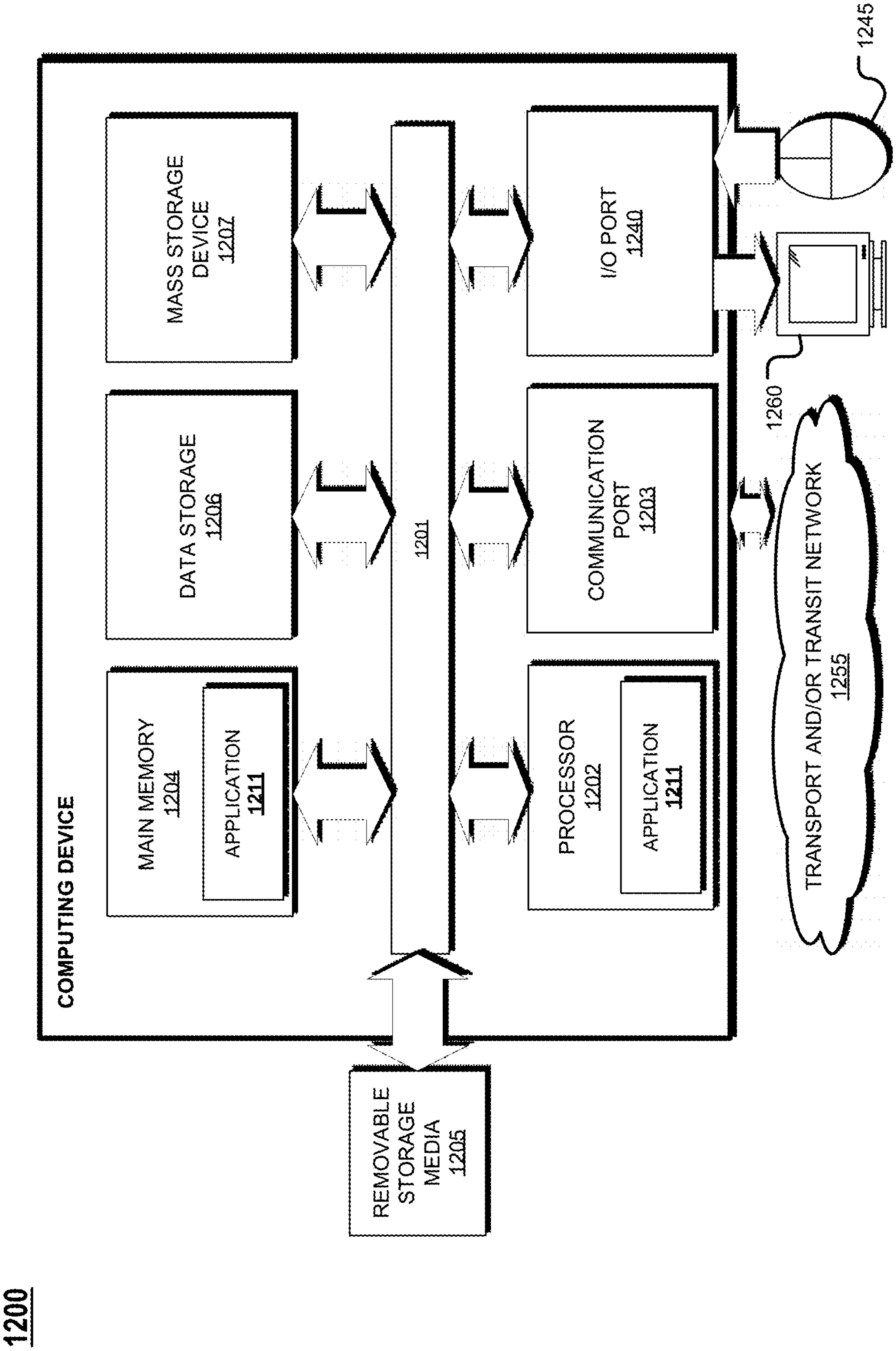
FIG. 7 is an exemplary simplified block diagram of a computing device that may be configured to implement various methodologies described herein.

Referring to FIG. 7, a computing device 1200 is illustrated which may be configured, via one or more of an application 1211 or computer-executable instructions, to execute functionality described herein associated with localization of seizure onset zone from independent components of resting state functional magnetic resonance. More particularly, in some embodiments, aspects of the predictive methods herein may be translated to software or machine-level code, which may be installed to and/or executed by the computing device 1200 such that the computing device 1200 is configured to such execute functionality as described herein. It is contemplated that the computing device 1200 may include any number of devices, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments, and the like.

The computing device 1200 may include various hardware components, such as a processor 1202, a main memory 1204 (e.g., a system memory), and a system bus 1201 that couples various components of the computing device 1200 to the processor 1202. The system bus 1201 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computing device 1200 may further include a variety of memory devices and computer-readable media 1207 that includes removable/non-removable media and volatile/nonvolatile media and/or tangible media, but excludes transitory propagated signals. Computer-readable media 1207 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computing device 1200. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 1204 includes computer storage media in the form of volatile/nonvolatile memory such as read only memory (ROM) and random access memory (RAM). A basic input/output system (BIOS), containing the basic routines that help to transfer information between elements within the computing device 1200 (e.g., during start-up) is typically stored in ROM. RAM typically contains data and/or program modules that are immediately accessible to and/or presently being operated on by processor 1202. Further, data storage 1206 in the form of Read-Only Memory (ROM) or otherwise may store an operating system, application programs, and other program modules and program data.

The data storage 1206 may also include other removable/non-removable, volatile/nonvolatile computer storage media. For example, the data storage 1206 may be: a hard disk drive that reads from or writes to non-removable, nonvolatile magnetic media; a magnetic disk drive that reads from or writes to a removable, nonvolatile magnetic disk; a solid state drive; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules, and other data for the computing device 1200.

A user may enter commands and information through a user interface 1240 (displayed via a monitor 1260) by engaging input devices 1245 such as a tablet, electronic digitizer, a microphone, keyboard, and/or pointing device, commonly referred to as mouse, trackball or touch pad. Other input devices 1245 may include a joystick, game pad, satellite dish, scanner, or the like. Additionally, voice inputs, gesture inputs (e.g., via hands or fingers), or other natural user input methods may also be used with the appropriate input devices, such as a microphone, camera, tablet, touch pad, glove, or other sensor. These and other input devices 1245 are in operative connection to the processor 1202 and may be coupled to the system bus 1201, but may be connected by other interface and bus structures, such as a parallel port, game port or a universal serial bus (USB). The monitor 1260 or other type of display device may also be connected to the system bus 1201. The monitor 1260 may also be integrated with a touch-screen panel or the like.

The computing device 1200 may be implemented in a networked or cloud-computing environment using logical connections of a network interface 1203 to one or more remote devices, such as a remote computer. The remote computer may be a personal computer, a server, a router, a network PC, a peer device or other common network node, and typically includes many or all of the elements described above relative to the computing device 1200. The logical connection may include one or more local area networks (LAN) and one or more wide area networks (WAN) but may also include other networks. Such networking environments are commonplace in offices, enterprise-wide computer networks, intranets and the Internet.

When used in a networked or cloud-computing environment, the computing device 1200 may be connected to a public and/or private network through the network interface 1203. In such embodiments, a modem or other means for establishing communications over the network is connected to the system bus 1201 via the network interface 1203 or other appropriate mechanism. A wireless networking component including an interface and antenna may be coupled through a suitable device such as an access point or peer computer to a network. In a networked environment, program modules depicted relative to the computing device 1200, or portions thereof, may be stored in the remote memory storage device.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a standalone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure the processor 1202, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

Computing systems or devices referenced herein may include desktop computers, laptops, tablets e-readers, personal digital assistants, smartphones, gaming devices, servers, and the like. The computing devices may access computer-readable media that include computer-readable storage media and data transmission media. In some embodiments, the computer-readable storage media are tangible storage devices that do not include a transitory propagating signal. Examples include memory such as primary memory, cache memory, and secondary memory (e.g., DVD) and other storage devices. The computer-readable storage media may have instructions recorded on them or may be encoded with computer-executable instructions or logic that implements aspects of the functionality described herein. The data transmission media may be used for transmitting data via transitory, propagating signals or carrier waves (e.g., electromagnetism) via a wired or wireless connection.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for automating independent component sorting for seizure onset zone localization, comprising:
- a processor in communication with a memory, the memory including instructions which, when executed, cause the processor to:
  - access resting state functional magnetic resonance imaging data;
  - access a plurality of expert derived rules for identifying noise in resting state functional magnetic resonance imaging data;
  - generate a plurality of independent components from the resting state functional magnetic resonance imaging data using independent components analysis, each independent component in the plurality of independent components including a plurality of slices;

categorize the plurality of independent components as noise independent components or non-noise independent components by:

accessing each slice in each independent component, applying the plurality of expert derived rules to each slice to generate a plurality of slice statistics, and categorizing each independent component as noise or non-noise based on the plurality of expert derived rules and the plurality of slice statistics across one or more slices in the plurality of slices; and identify a plurality of seizure onset zone independent components within the non-noise independent components using an artificial intelligence (AI) model, the plurality of seizure onset zone independent components accommodating localization of seizure onset zones.

2. The system of claim 1, wherein the AI model includes a classifier that uses a maximum likelihood-based clustering mechanism for identifying seizure onset zone independent components by:

accessing a plurality of features for classifying seizure onset zone independent components, generating a plurality of weights, each weight in the plurality of weights corresponding to a feature in the plurality of features, and applying the plurality of weights to the plurality of non-noise independent components to identify seizure onset zone independent components.

3. The system of claim 1, wherein the processor:

applies the plurality of expert derived rules in a sequential order to each slice, generates a score for indicating noise, categories the slice as noise or non-noise based on the score, and removes the slice from the plurality of slices if the slice is categorized as noise.

4. The system of claim 1, the memory further including instructions, which, when executed, cause the processor to:

generate spatial and temporal markers based on the plurality of independent components for use by the AI model.

5. The system of claim 1, wherein the expert derived rules for identifying noise in resting state functional magnetic resonance imaging data include:

a. a rule specifying the independent component exceeding a predetermined number of small voxel clusters, b. cluster peaks in white matter, c. a high overlap with white matter, cerebrospinal fluid, or blood vessels, d. a crescent shape aligning with a brain boundary, or e. a sudden change in oscillation pattern.

6. The system of claim 1, the memory further including instructions, which, when executed, cause the processor to:

access a parameter for a quantity of slices to select, sort the plurality of slices for each independent component in based on a cluster size of the slice, select a number of slices based on the parameter, and categorize the independent component as noise if the number of slices categorized as noise exceeds a threshold.

7. The system of claim 1, wherein the slice statistics include:

a. a cluster size, b. a percentage overlap of each cluster with a brain boundary, c. a percentage overlap of each cluster with blood vessels, and d. a percentage overlap of each cluster with white matter.

8. A system for automated seizure onset localization, comprising:

a processor, configured to execute a predetermined model defining operations to:

access resting state functional magnetic resonance imaging data defining a plurality of independent components generated using independent component analysis, each independent component comprising a plurality of slices;

remove one or more noise independent components using fMRI noise-related biomarkers by application of a plurality of expert-derived rules in a sequential waterfall order to the slices of the independent components to generate slice statistics including a cluster size and percentage overlap of each cluster with a brain boundary, white matter and blood vessels, and categorization of each independent component as a noise independent component or a non-noise independent component based on the slice statistics; and implement seizure onset localization (SOZ) markers through a classifier that encodes expert knowledge in spatial and temporal seizure onset zone (SOZ) markers to determine SOZ localizing independent components from the plurality of independent components.

9. The system of claim 8, wherein the processor as configured localizes a seizure onset zone (SOZ) from independent components (IC) of resting state functional magnetic resonance imaging (rs-fMRI) to improve surgical outcomes in children with Drug Resistant Epilepsy (DRE).

10. The system of claim 8, wherein the processor is further configured to classify an independent component from the plurality of independent components as noise, by executing steps of:

(a) voxel cluster detection to derive voxel clusters in each independent component slice associated with the imaging data, (b) brain boundary detection to search for a contour that encompasses all other contours in the brain, (C) white matter detection to discard blood vessels and cerebrospinal fluid in white matter contour, and (d) blood vessel detection for major basal-region blood vessels presented as low intensity contours.

11. The system of claim 8, wherein for seizure onset localization the processor is further configured to execute SOZ classification convolutional neural network (CNN) based deep learning (DL) based on a maximum likelihood-based clustering mechanism.

12. The system of claim 11, wherein hypertuning is applied by the processor to derive an optimal set of values of hyperparameters for the convolutional neural network (CNN) based deep learning (DL).

13. The system of claim 8, wherein the predetermined model is unsupervised thus requiring not prior dataset for training and classifies ICs by encoding expert knowledge, defines a waterfall technique to purge noise ICs, and uses SOZ specific spatial and temporal markers in a maximum likelihood-based clustering to further classify the ICs into RSN and SOZ.

14. The system of claim 13, wherein the predetermined model applies clustering that is unsupervised and is devoid of training with prior data to tune parameters.

15. A method, comprising:

accessing resting state functional magnetic resonance imaging data;

accessing a plurality of expert derived rules for identifying noise in resting state functional magnetic resonance imaging data;

generating a plurality of independent components from the resting state functional magnetic resonance imaging data using independent components analysis, each independent component in the plurality of independent components including a plurality of slices;

categorizing the plurality of independent components as noise independent components or non-noise independent components; and identifying a plurality of seizure onset zone independent components within the non-noise independent components using an artificial intelligence (AI) model, the plurality of seizure onset zone independent components accommodating localization of seizure onset zones.

16. The method of claim 15, further comprising, to categorize the plurality of independent components as noise independent components or non-noise independent components:

accessing each slice in each independent component, applying the plurality of expert derived rules to each slice to generate a plurality of slice statistics, and categorizing each independent component as noise or non-noise based on the plurality of expert derived rules and the plurality of slice statistics across one or more slices in the plurality of slices.

17. The method of claim 15, wherein the AI model includes a classifier that uses a maximum likelihood-based clustering mechanism for identifying seizure onset zone independent components.

18. The method of claim 15, further comprising:

applying the plurality of expert derived rules in a sequential order to each slice, generating a score for indicating noise, categorizing the slice as noise or non-noise based on the score, and removing the slice from the plurality of slices if the slice is categorized as noise.

19. The method of claim 15, further comprising:

generating spatial and temporal markers based on the plurality of independent components for use by the AI model.

20. The method of claim 15, wherein the AI model is unsupervised and identifies internal components (ICs) by encoding expert knowledge, defines a waterfall technique to purge noise ICs, and uses seizure onset zone (SOZ) specific spatial and temporal markers with maximum likelihood-based clustering.

* * * * *